United States Patent
Church et al.

(10) Patent No.: US 10,640,826 B2
(45) Date of Patent: *May 5, 2020

(54) SPATIAL SEQUENCING OF NUCLEIC ACIDS USING DNA ORIGAMI PROBES

(71) Applicant: President and Fellows of Harvard College, Cambridge, MA (US)

(72) Inventors: George M. Church, Brookline, MA (US); Richard C. Terry, Carlisle, MA (US); Frederic Vigneault, Ashland, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/886,163

(22) Filed: Feb. 1, 2018

(65) Prior Publication Data

US 2018/0230533 A1    Aug. 16, 2018

Related U.S. Application Data

(63) Continuation of application No. 14/402,795, filed as application No. PCT/US2013/044241 on Jun. 5, 2013, now Pat. No. 9,914,967.

(60) Provisional application No. 61/655,528, filed on Jun. 5, 2012.

(51) Int. Cl.
*C12Q 1/6874* (2018.01)
*C12Q 1/6869* (2018.01)

(52) U.S. Cl.
CPC ........ *C12Q 1/6874* (2013.01); *C12Q 1/6869* (2013.01)

(58) Field of Classification Search
CPC ............................ C12Q 1/6874; C12Q 1/6869
See application file for complete search history.

(56) References Cited

U.S. PATENT DOCUMENTS

| | | | |
|---|---|---|---|
| 4,123,610 A | 10/1978 | Summerton et al. | |
| 4,844,617 A | 7/1989 | Kelderman et al. | |
| 4,981,985 A | 1/1991 | Kaplan et al. | |
| 5,563,056 A | 10/1996 | Swan et al. | |
| 5,594,235 A | 1/1997 | Lee | |
| 5,830,708 A | 11/1998 | Naughton | |
| 7,323,305 B2 | 1/2008 | Leamon et al. | |
| 7,473,767 B2 | 1/2009 | Dimitrov | |
| 8,501,459 B2 | 8/2013 | Chen et al. | |
| 8,551,710 B2 | 10/2013 | Bernitz et al. | |
| 9,217,151 B2 | 12/2015 | Yin et al. | |
| 2002/0015952 A1 | 2/2002 | Anderson et al. | |
| 2002/0155989 A1* | 10/2002 | Efimov .................. | C07H 21/00 544/243 |
| 2003/0148335 A1 | 8/2003 | Shen et al. | |
| 2004/0077014 A1 | 4/2004 | Becker | |
| 2004/0248144 A1 | 12/2004 | Mir | |
| 2004/0259190 A1 | 12/2004 | Naughton | |
| 2005/0106629 A1 | 5/2005 | McGrath et al. | |
| 2005/0147981 A1 | 7/2005 | Yamakawa et al. | |
| 2005/0233318 A1 | 10/2005 | Chee et al. | |
| 2006/0024711 A1 | 2/2006 | Lapidus et al. | |
| 2006/0077536 A1 | 4/2006 | Bromage et al. | |
| 2006/0177833 A1 | 8/2006 | Brenner | |
| 2006/0234261 A1 | 10/2006 | Pierce et al. | |
| 2006/0248349 A1 | 11/2006 | Rathjen et al. | |
| 2006/0292611 A1 | 12/2006 | Berka et al. | |
| 2007/0020650 A1 | 1/2007 | Kahvejian | |
| 2007/0087362 A1 | 4/2007 | Church et al. | |
| 2007/0117109 A1 | 5/2007 | Rothemund | |
| 2007/0117177 A1 | 5/2007 | Luo et al. | |
| 2007/0206275 A1 | 9/2007 | Hemmer et al. | |
| 2008/0176769 A1 | 7/2008 | Rank et al. | |
| 2009/0005259 A1 | 1/2009 | Drmanac | |
| 2009/0208965 A1 | 8/2009 | Tafas et al. | |
| 2009/0246879 A1 | 10/2009 | Drmanac et al. | |
| 2010/0009868 A1 | 1/2010 | Yan et al. | |
| 2010/0047924 A1 | 2/2010 | Webster et al. | |
| 2010/0223276 A1 | 9/2010 | Al-Shameri et al. | |
| 2010/0268478 A1 | 10/2010 | Andregg et al. | |
| 2011/0020291 A1 | 1/2011 | Banerjee et al. | |
| 2011/0086774 A1 | 4/2011 | Dunaway | |
| 2011/0092376 A1 | 4/2011 | Colston, Jr. et al. | |
| 2011/0245111 A1 | 10/2011 | Chee | |
| 2011/0257031 A1 | 10/2011 | Bodeau et al. | |
| 2011/0294135 A1 | 12/2011 | Carlson | |
| 2012/0040397 A1 | 2/2012 | Luo et al. | |
| 2012/0122712 A1 | 5/2012 | Goldstein | |
| 2013/0017229 A1 | 1/2013 | Mooney et al. | |
| 2013/0245096 A1 | 9/2013 | Abitbol | |
| 2014/0049632 A1 | 2/2014 | Hemmer | |

(Continued)

FOREIGN PATENT DOCUMENTS

| | | |
|---|---|---|
| KR | 20080003402 A | 1/2008 |
| WO | 9746704 A1 | 12/1997 |

(Continued)

OTHER PUBLICATIONS

Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.

Benner et al. "Gene Expression analysis by massively parallel signature sequencing (MPSS) on microbead arrays". Nature Biotechnology, vol. 18, pp. 630-634 (Jun. 31, 2000).

Brenner, et al. "Gene expression analysis by massively parallel signature sequencing (MPSS) on microbead arrays". Nature Biotechnology vol. 18, pp. 630-634 (2000) doi:10.1038/76469.

Eliscovich et al. mRNA on the move: The road to its biological destiny. Journal of Biological Chemistry, vol. 288, No. 28, pp. 20361-20368, Jul. 2013, in press May 2013 (Year: 2013).

Extended European Seach Report issued in corresponding European Application No. 12860433.7, dated Aug. 13, 2015.

(Continued)

*Primary Examiner* — Narayan K Bhat

(74) *Attorney, Agent, or Firm* — Banner & Witcoff, Ltd.

(57) ABSTRACT

A method of sequencing nucleic acids is provided using DNA origami as a barcode for a nucleic acid probe.

19 Claims, 13 Drawing Sheets

Specification includes a Sequence Listing.

(56) References Cited

U.S. PATENT DOCUMENTS

| | | |
|---|---|---|
| 2014/0087378 A1 | 3/2014 | Chatre et al. |
| 2014/0220587 A1 | 8/2014 | Green, Jr. et al. |
| 2015/0133319 A1 | 5/2015 | Fu et al. |
| 2016/0024555 A1 | 1/2016 | Church et al. |
| 2016/0265046 A1 | 9/2016 | Zhang et al. |
| 2017/0212983 A1 | 7/2017 | Cai et al. |

FOREIGN PATENT DOCUMENTS

| | | | |
|---|---|---|---|
| WO | 01/26708 | A1 | 4/2001 |
| WO | 01/37266 | A1 | 5/2001 |
| WO | 2004/104645 | A2 | 12/2004 |
| WO | 2007086900 | A2 | 8/2007 |
| WO | 2007/121489 | A2 | 10/2007 |
| WO | 2008069973 | A2 | 6/2008 |
| WO | 2009046149 | A1 | 4/2009 |
| WO | 2010080134 | A1 | 7/2010 |
| WO | 2011/143583 | A1 | 11/2011 |
| WO | 2012005595 | A2 | 1/2012 |
| WO | 2012/058638 | A2 | 5/2012 |
| WO | 2012150035 | A1 | 11/2012 |
| WO | 2013/055995 | A2 | 4/2013 |
| WO | 2014/0163886 | A1 | 10/2014 |
| WO | 2014/182528 | A2 | 11/2014 |
| WO | 2015/118029 | A1 | 8/2015 |

OTHER PUBLICATIONS

Ginart, P et al. RNA Sequencing In Situ. Nat Biotechnol. Jun. 2014, vol. 32, No. 6; pp. 543-544; DOI: 10.1038/nbt.2921.

Grompe (1993) Nature Genetics DOI: 10.1038/ng1093-111.

Han et al. "Quantum-dot-tagged microbeads for multiplexed optical coding of biomolecules". Nature Biotechnology, vol. 19, 99. 631-635 (Jul. 31, 2001).

International Search Report and Written Opinion issued in corresponding International Application No. PCT/US2012/071398, dated Apr. 8, 2013.

Jambhekar et al. Cis-acting determinants of asymmetric, cytoplasmic RNA transport. RNA, vol. 13, pp. 625-642, 2007 (Year: 2007).

Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).

Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.

Matlin et al. Spatial expression of the genome: The signal hypothesis at forty. Nature Reviews. Molecular Cell Biology, vol. 12, No. 5, pp. 333-340, May 2011, Epub Apr. 2011. (Year 2011).

Meeks et al. Characterization of genes encoding poly(A) polymerases in plants: Evidence for duplication and functional specialization. PLoS One, vol. 4, No. 11, e8082, Nov. 2009, printed as pp. 1/10-10/10. (Year 2009).

Office Action issued for corresponding European Patent Application No. 12780609.9, dated Sep. 23, 2015.

Polidoros et al. Rolling circle amplification—RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).

Saliba, AE et al. Single-Cell RNA-SEQ: Advances and Future Challenges. Nucleic Acids Res. Jul. 22, 2014, vol. 42, No. 14; pp. 8845-8860; DOI: 10.1093/nar/gku555.

Seo, et al. Four-color DNA sequencing by synthesis on a chip using photocleavable fluorescent nucleotides. Proceeding of the National Academy of Sciences, Apr. 2005, 102 (17) 5926-5931.

Singer-Kruger et al. Here, there, everywhere. RNA Biology, vol. 11, No. 8, pp. 1031-1039, Aug. 2014. (Year: 2014).

Thisse et al. "High-Resolution in situ hybridization to whole-mount zebrafish embryos" 2008. Nature Protocols. vol. 3 No. 1 pp. 59-69. Doi:10.1038/nprot.2007.514.

Thisse et al. 2008 Nature protocols vol. 3 No. 1 pp. 59-69. Doi:10.1038/nprot.2007.514.

Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year 2004).

Weis et al. Protein targeting to subcellular organelles via mRNA localization. Biochimica et Biophysica Acta, vol. 1833, pp. 260-273, 2013, available online Apr. 2012 (Year 2012).

Dec. 18, 2014 (PCT) International Preliminary Report—App PCT/US2013/044241.

Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.

Cao, Yi et al.,"In-situ immuno-PCR to detect antigens," The Lancet, Sep. 16, 2000, pp. 1002-1003, vol. 356.

Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retrieved from the Internet: URL:http://dspace.mit.edu/bitstream/handle/1721.1/107103/971494098-MIT.pdf?sequence=1 [retrieved on Feb. 20, 2019].

Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.

Extended European Search Report dated May 13, 2019 for EP Application No. 16862929.3.

Extended European Search Report dated May 21, 2019 for European Application No. 16862945.9.

International Search Report and Written Opinion based on PCT/US2018/027583 dated Jun. 29, 2018.

Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.

Sano, Takeshi et al. "Immuno-PCR: Very Sensitive Antigen Detection by Means of Specific Antibody-DNA Conjugates," Science, Oct. 2, 1992, pp. 120-122, vol. 258.

Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.

Soderberg, Ola et al.,"Direct observation of individual endogenous protein complexes in situ by proximity ligation," Nature Methods, Dec. 2006, pp. 995-1000, vol. 3, No. 12, Nature Publishing Group.

Choi, Harry M.T. et al., "Next-Generation in Situ Hybridization Chain Reaction: Higher Gain, Lower Cost, Greater Durability" ACS NANO, vol. 8, No. 5, May 27, 2014 (May 27, 2014), pp. 4284-4294, XP055409053, US.

Extended European Search Report issued for EP Application No. 17790240.0 dated Sep. 4, 2019.

Ravan, Hadi, et al. "Isothermal RNA detection through the formation of DNA concatemers contiaining HRP-mimicking DNAzymes on the surface of gold nanoparticles", Biosensors and Bioelectronics, Elsevier Science LTD. UK, Amsterdam, NL, vol. 80, Jan. 18, 2016 (Jan. 18, 2016), pp. 67-73, XP029441324.

* cited by examiner

CCGTAAGGTAGGTAGTCAAC (SEQ ID NO: 23)

```
       C G     A T    AT
CY5-T A        CY3-G C   TR-T A
       A T    TA
       ATGGCTCAAGAAGGCGTATA
```

CCGTAAGGTAGGTAGTCAAC (SEQ ID NO: 24)

```
       C G     A T    AT
       FITC-T A   CY3-G C   TR-T A
       T A
       G C
       C G
       G C
       ATGGCTCAAGAAGGCGTATA
```

6bp 1.8nm Origami Probe
15bp 4.5nm Random Primer
Ligation Junction

NNNNNNNNNNNNNN*CCAGTN*   NNNNNNNNNNNNNN*GAACGN*   NNNNNNNNNNNNNN*TTAGTN*
(SEQ ID NO: 25)

....*TCTAGGCTACGGTAGGTCAGTCCAGTGGTAGCAGTCGGTCGATCCGTGGCAGTCCGTGATGCAATCGTCGGGAAATGCCTTGAGACACCTAGTTGGTAATCATTAGAGCGGCTCAGATCGC*.....

Stretched ssDNA (SEQ ID NO: 22)

FIG. 2

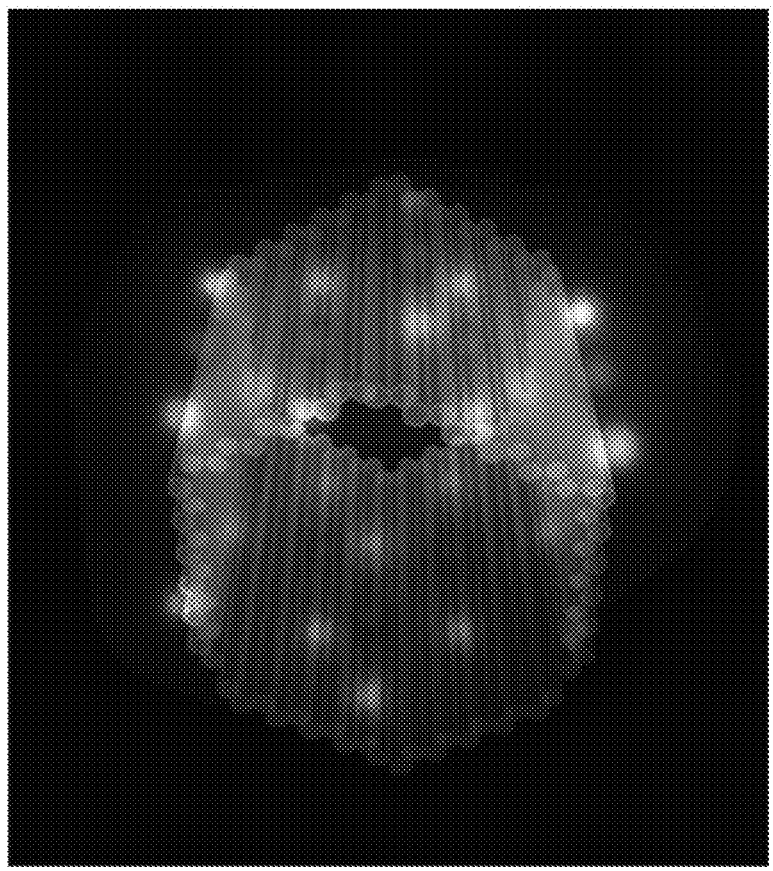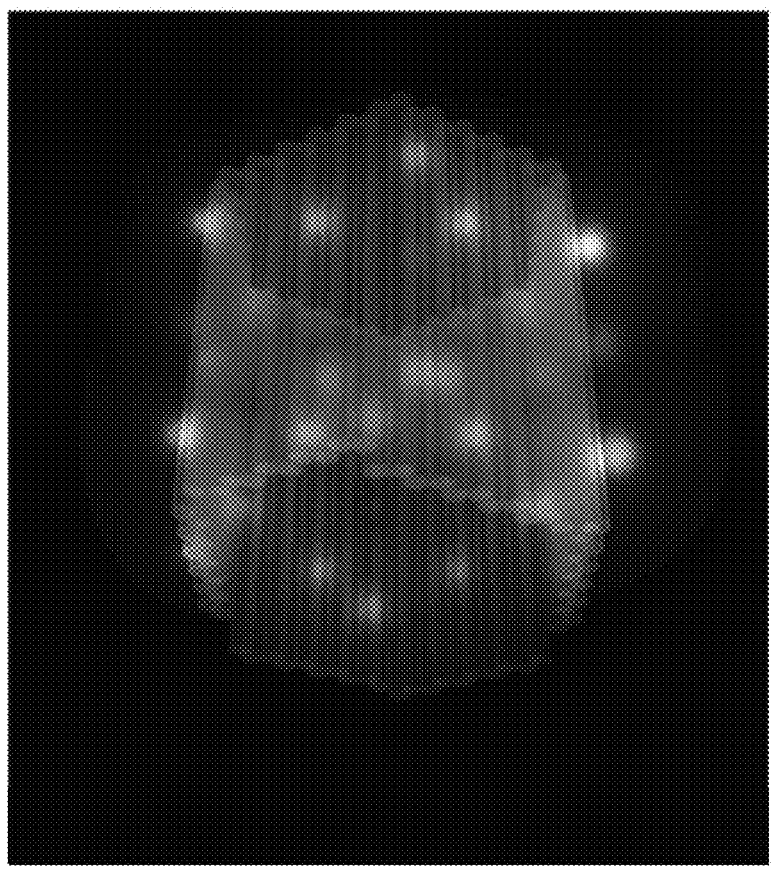
FIG. 3

SPATIAL SEQUENCING OF NUCLEIC ACIDS USING DNA ORIGAMI PROBES

RELATED APPLICATION

This application is a continuation application which claims priority to U.S. patent application Ser. No. 14/402,795, filed on Nov. 21, 2014, which is a National Stage Application under 35 U.S.C. 371 of co-pending PCT application PCT/US2013/044241 designating the United States and filed Jun. 5, 2013; which claims the benefit of U.S. provisional application No. 61/655,528 and filed Jun. 5, 2012 each of which are hereby incorporated by reference in their entireties.

STATEMENT OF GOVERNMENT INTERESTS

This invention was made with Government support under NIH Grant Number 5P50HG005550-02. The Government has certain rights in the invention.

FIELD

The present invention relates to methods of sequencing nucleic acids.

BACKGROUND

Sequencing methods are known. See for example Shendure et al., Accurate multiplex polony sequencing of an evolved bacterial genome, *Science*, vol. 309, p. 1728-32. 2005; Drmanac et al., Human genome sequencing using unchained base reads on self-assembling DNA nanoarrays, *Science*, vol. 327, p. 78-81. 2009; McKernan et al., Sequence and structural variation in a human genome uncovered by short-read, massively parallel ligation sequencing using two-base encoding, *Genome Res.*, vol. 19, p. 1527-41. 2009; Rodrigue et al., Unlocking short read sequencing for metagenomics, *PLoS One*, vol. 28, e11840. 2010; Rothberg et al., An integrated semiconductor device enabling non-optical genome sequencing, *Nature*, vol. 475, p. 348-352. 2011; Margulies et al., Genome sequencing in microfabricated high-density picolitre reactors, *Nature*, vol. 437, p. 376-380. 2005; Rasko et al. Origins of the *E. coli* strain causing an outbreak of hemolytic-uremic syndrome in Germany, *N. Engl. J. Med.*, Epub. 2011; Hutter et al., Labeled nucleoside triphosphates with reversibly terminating aminoalkoxyl groups, *Nucleos. Nucleot. Nucl.*, vol. 92, p. 879-895. 2010; Seo et al., Four-color DNA sequencing by synthesis on a chip using photocleavable fluorescent nucleotides, *Proc. Natl. Acad. Sci. USA.*, Vol. 102, P. 5926-5931 (2005); Olejnik et al.; Photocleavable biotin derivatives: a versatile approach for the isolation of biomolecules, *Proc. Natl. Acad. Sci. U.S.A.*, vol. 92, p. 7590-7594. 1995; U.S. Pat. No. 5,750,34; US 2009/0062129 and US 2009/0191553.

SUMMARY

Embodiments of the present disclosure are directed to methods for determining the sequence of nucleotides in a target polynucleotide using sequencing by ligation and/or sequencing by hybridization. Certain aspects include hybridizing and/or ligating a probe having a spatially distinct nucleic acid structure to a nucleic acid template, such as a single stranded nucleic acid template. According to one aspect, the spatially distinct nucleic acid structure is representative of one or more or all of the nucleotides in the oligonucleotide probe. According to one aspect, the spatially distinct nucleic acid structure is representative of a plurality of the nucleotides in the oligonucleotide probe. According to one aspect, the spatially distinct nucleic acid structure is representative of all of the nucleotides in the oligonucleotide probe.

Embodiments of the present disclosure are directed to methods for determining the sequence of nucleotides in a target polynucleotide using sequencing by ligation and/or sequencing by hybridization. Certain aspects include hybridizing and/or ligating a probe having a non-naturally occurring two dimensional or three dimensional nucleic acid structure to a nucleic acid template, such as a single stranded nucleic acid template. According to one aspect, the non-naturally occurring two dimensional or three dimensional nucleic acid structure is representative of one or more or all of the nucleotides in the oligonucleotide probe. According to one aspect, the non-naturally occurring two dimensional or three dimensional nucleic acid structure is representative of a plurality of the nucleotides in the oligonucleotide probe. According to one aspect, the non-naturally occurring two dimensional or three dimensional nucleic acid structure is representative of all of the nucleotides in the oligonucleotide probe.

Embodiments of the present disclosure are directed to methods for determining the sequence of nucleotides in a target polynucleotide using sequencing by ligation and/or sequencing by hybridization. Certain aspects include hybridizing and/or ligating a probe having a visually resolvable or visually distinguishable two dimensional or three dimensional nucleic acid structure to a nucleic acid template, such as a single stranded nucleic acid template. According to one aspect, the visually resolvable or visually distinguishable two dimensional or three dimensional nucleic acid structure is representative of one or more or all of the nucleotides in the oligonucleotide probe. According to one aspect, the visually resolvable or visually distinguishable two dimensional or three dimensional nucleic acid structure is representative of a plurality of the nucleotides in the oligonucleotide probe. According to one aspect, the visually resolvable or visually distinguishable two dimensional or three dimensional nucleic acid structure is representative of all of the nucleotides in the oligonucleotide probe.

Embodiments of the present disclosure are directed to methods for determining the sequence of nucleotides in a target polynucleotide using sequencing by ligation and/or sequencing by hybridization. Certain aspects include hybridizing and/or ligating a probe having a nucleic acid origami structure to a nucleic acid template, such as a single stranded nucleic acid template. According to one aspect, the nucleic acid origami structure is representative of one or more or all of the nucleotides in the oligonucleotide probe. According to one aspect, the nucleic acid origami structure is representative of a plurality of the nucleotides in the oligonucleotide probe. According to one aspect, the nucleic acid origami structure is representative of all of the nucleotides in the oligonucleotide probe.

According to certain aspects, spatially distinct nucleic acid structures, non-naturally occurring two dimensional or three dimensional nucleic acid structures, and visually resolvable or visually distinguishable two dimensional or three dimensional nucleic acid structures may be collectively referred to herein as nucleic acid origami structures.

According to certain aspects, a set of probes can be designed with nucleic acid origami structures being geometrically distinct or geometrically unique within the set of probes such that the nucleic acid origami structure corresponds to a known one or more or all of the nucleotides in a particular oligonucleotide probe. In this manner, the geometrically distinct or geometrically unique nucleic acid origami structure is a barcode for the one or more or all of the nucleotides in a particular oligonucleotide probe. By determining the structure of the geometrically distinct or geometrically unique nucleic acid origami structure, the corresponding one or more or all of the nucleotides in the oligonucleotide probe can be identified. According to one aspect, the nucleic acid origami structure is visually distinct. According to one aspect, the nucleic acid origami structure is spatially distinct. Since the one or more or all of the nucleotides in the oligonucleotide probe can be identified, the corresponding complementary one or more or all of the nucleotides in the nucleic acid template can be identified. Using a plurality of oligonucleotide probes having geometrically distinct or geometrically unique nucleic acid origami structures which can be identified, the sequence of the nucleotides in the nucleic acid template can be determined using sequencing by ligation methods or using sequencing by hybridization methods.

According to one aspect, the nucleic acid origami structure may include one or more detectable moieties or barcodes. According to this aspect, the one or more detectable moieties or barcodes correspond to a known one or more or all of the nucleotides in a particular oligonucleotide probe. One such nucleotide is the terminal hybridized nucleotide in the oligonucleotide probe. According to this exemplary aspect, a set of oligonucleotide probes include an A, C, G, or T as the terminal hybridized nucleotide with a different detectable moiety or barcode corresponding to one of A, C, G, or T. Since the detectable moiety or barcode corresponds to a known nucleotide, detection of the detectable moiety or barcode confirms hybridization and/or ligation of a particular oligonucleotide probe from within a set of oligonucleotide probes and the identity of the terminal hybridized nucleotide of the oligonucleotide probe. In addition, certain embodiments of the present disclosure discussed herein utilize different detectable moieties or barcodes capable of identifying two or more different oligonucleotides at the same time, as the different detectable moieties or barcodes are capable of differentiating between different oligonucleotides. As an example, detectable moieties may have wavelengths different enough to be distinguishable. Different barcodes may be differentiated or distinguished using methods known to those of skill in the art. According to this aspect, as many oligonucleotides could be identified as there are distinguishable detectable moieties or barcodes. According to an additional aspect, a particular detectable moiety or barcode can represent one or more or all of the oligonucleotides in an oligonucleotide probe. Accordingly, the use of a detectable moiety or barcode may be used for any nucleotide or combination of nucleotides within the oligonucleotide probe and is not limited to the terminal hybridized nucleotide.

Accordingly, one or more detectable moieties or barcodes can be attached to a single nucleic acid origami structure or geometrically non-distinct or geometrically non-unique nucleic acid origami structure serving as a scaffold for the one or more detectable moieties or barcodes. The detectable moiety or barcode can be detected or identified. According to one aspect, the one or more detectable moieties or barcodes attached to a nucleic acid origami structure may render the nucleic acid origami structure unique within a set of probes. For example, a unique combination of detectable moieties or detectable moieties with a unique placement on the nucleic acid origami structure can allow the nucleic acid origami structure to uniquely identify a known one or more or all of the nucleotides in an oligonucleotide probe. In this manner, only a single nucleic acid origami structure need be prepared for each of the oligonucleotide probes in a set since a unique barcode or unique detectable moiety or combination of detectable moieties or unique location of a detectable moiety or moieties attached to each nucleic acid origami structure within the probe set will render the nucleic acid origami structure uniquely representative for a known one or more or all of the nucleotides in a particular oligonucleotide probe. By identifying the one or more detectable moieties or barcodes attached to the nucleic acid origami structure, the corresponding one or more or all of the nucleotides in the oligonucleotide probe can be identified. Since the one or more or all of the nucleotides in the oligonucleotide probe can be identified, the corresponding complementary one or more or all of the nucleotides in the nucleic acid template can be identified. Using a plurality of oligonucleotide probes having nucleic acid origami structures with one or more detectable moieties or barcodes, the sequence of the nucleotides in the nucleic acid template can be determined using sequencing by ligation methods or using sequencing by hybridization methods.

According to certain aspects, one or more or all of the nucleotides in a particular oligonucleotide probe can be identified using geometrically distinct or geometrically unique nucleic acid origami structures or detectable moieties or barcodes or a combination thereof. In this manner, nucleic acid origami structures need not be geometrically distinct or geometrically unique for a given set of probes. A single nucleic acid origami structure design or a plurality of nucleic acid origami structure designs can be used with unique barcodes or detectable moieties to identify corresponding known one or more or all of the nucleotides in a particular oligonucleotide probe.

The nucleic acid origami structure may include a probe hybridization site corresponding to a known one or more or all of the nucleotides in the oligonucleotide probe. A probe with a detectable moiety is then hybridized to the probe hybridization site and the detectable moiety is detected. According to certain aspects, a one or more or all of the nucleotides in the oligonucleotide probe is identified by detecting a corresponding detectable moiety and, accordingly, the corresponding complementary one or more or all of the nucleotides in the nucleic acid template can be identified. According to one aspect, the nucleic acid origami structure may include a probe hybridization site which can be hybridized with a probe including a spatially detectable moiety. In this manner, the probe with a spatially detectable moiety is a barcode for the oligonucleotide probe.

According to still certain aspects, the nucleic acid origami structure may be detached from the oligonucleotide probe and an additional oligonucleotide probe having a nucleic acid origami structure may then be ligated and a one or more or all of the nucleotides in the oligonucleotide probe can be identified using the nucleic acid origami structure as described herein. According to further aspects, an oligonucleotide probe may include a nucleic acid origami structure flanked on either side by an oligonucleotide probe suitable for hybridization and ligation. According to this aspect, a dual probe structure with a nucleic acid origami structure is provided.

According to a certain aspect, a nucleic acid template is provided for sequencing. The nucleic acid template may be either single stranded or double stranded. If single stranded, one or more sequencing primers may be hybridized to the single stranded nucleic acid template. The sequencing primers may be specific, semi-random or random. The sequencing primers hybridized to the single stranded nucleic acid template allow for hybridization and ligation of probes with nucleic acid origami structures. According to an additional embodiment, if the nucleic acid template is double stranded, one strand will serve as the template and portions of the complementary strand will be removed using methods known to those of skill in the art and hybridized portions will remain which serve as sequencing primers. The hybridized portions of the complementary strand allow for hybridization and ligation of oligonucleotide probes with nucleic acid origami structures.

According to a certain aspect, a nucleic acid template to be sequenced may be stretched, straight or partially straight. For example, a nucleic acid template to be sequenced may be stretched into an elongated position, drawn out or elongated spatially, straightened or partially straightened. The nucleic acid template may be maintained in a stretched, elongated, drawn out, straight or partially straight position during one or more steps of the sequencing methods described herein. For example, a single stranded nucleic acid template may be attached to a substrate at either the 5' or 3' end and the nucleic acid template may be stretched, stretched into an elongated position, drawn out, elongated spatially, straightened or partially straightened under force, such as a physical force to produce a nucleic acid template that is stretched, elongated, straight, or partially straight. One or more sequencing primers are hybridized along the length of the stretched, elongated, straight or partially straight nucleic acid template. According to an alternate aspect, one or more sequencing primers may be hybridized to the nucleic acid template and then the nucleic acid template with the sequencing primers hybridized thereto may be stretched, elongated, straightened or partially straightened to produce a stretched, elongated, straight or partially straight nucleic acid template sequencing primer construct. Methods of stretching or straightening nucleic acids such as DNA are known. See for example Das et al., *Nucleic Acids Research,* 2010, 1-8, doi:10.1093/nar/gkq673, Guan et al., PNAS, vol. 102, no. 51, pp. 18321-18325 (2005) and Allemand et al., Biophysical Journal, vol. 73, pp. 2064-2070 (1997) (describing combing of DNA) each of which are hereby incorporated by reference in its entirety.

One or more oligonucleotide probes having nucleic acid origami structures are hybridized to the stretched, elongated, straight or partially straight template nucleic acid sequence. According to an alternate aspect, one or more oligonucleotide probes having nucleic acid origami structures are hybridized to a template nucleic acid sequence, and then the construct is stretched, elongated, straightened or partially straightened to form a stretched, elongated, straight or partially straight template nucleic acid sequence and hybridized probe construct.

One or more oligonucleotide probes having nucleic acid origami structures are hybridized to the straight or partially straight template nucleic acid sequence and ligated to an adjacent sequencing primer. According to an alternate aspect, one or more oligonucleotide probes having nucleic acid origami structures are hybridized to a template nucleic acid sequence and ligated to an adjacent sequencing primer to form a construct, and then the construct is stretched, elongated, straightened or partially straightened to form a stretched, elongated, straight or partially straight template nucleic acid sequence and hybridized and ligated probe construct.

According to one aspect, the template nucleic acid sequence is imaged or otherwise analyzed to identify the nucleic acid origami structures or detectable moieties or barcodes attached thereto. In this manner, the known one or more or all of the nucleotides in a particular oligonucleotide probe corresponding to a unique nucleic acid origami structure or detectable moiety or barcode can be identified. According to an additional aspect, the stretched, elongated, straight or partially straight template nucleic acid sequence with the oligonucleotide probes having nucleic acid origami structures is imaged or otherwise analyzed to identify the nucleic acid origami structures or detectable moieties or barcodes attached thereto. In this manner, the known one or more or all of the nucleotides in a particular oligonucleotide probe corresponding to a unique nucleic acid origami structure or detectable moiety or barcode can be identified.

According to the present disclosure, cycles of ligation and detection may be carried out along the length of the template nucleic acid in either the 5' to 3' direction or the 3' to 5' direction. Then, the process may be repeated starting again from either the 5' or 3' direction to identify additional nucleotides in the template nucleic acid. The process may be repeated until some, a plurality or all of the nucleotides in the template nucleic acid are identified as desired. According to an additional aspect, cycles of ligation and detection may be carried out in both the 5' to 3' direction and the 3' to 5' direction in parallel. According to one aspect, nucleotides may be identified as a result of ligations at the 5' end or as a result of ligations at the 3' end or both.

According to one aspect, a sequencing primer is hybridized to a single stranded nucleic acid template. An oligonucleotide probe is hybridized to the single stranded nucleic acid template and ligated to the sequencing primer to form an extended hybridized sequence. According to one aspect of the present disclosure, the oligonucleotide probe includes a nucleic acid origami structure. One feature of the nucleic acid origami structure is that it may prevent or inhibit or block multiple ligations of the oligonucleotide probe such that a single ligation occurs in a single cycle. Another feature of the nucleic acid origami structure is that it facilitates perfectly matched hybridization of the oligonucleotide probe as the nucleic acid origami structure includes a nucleotide directly attached to the oligonucleotide probe and where such nucleotide does not hybridize to the template nucleic acid. Accordingly, an additional feature of the nucleic acid origami structure is that it may be immediately adjacent and/or attached to the terminal hybridized nucleotide in the oligonucleotide probe such that the oligonucleotide probe is hybridized to the single stranded nucleic acid template while the nucleic acid origami structure is not. Such a combination of an oligonucleotide probe and nucleic acid origami structure reduces bias insofar as the number of nucleotides in the oligonucleotide probe hybridized to the template nucleic acid is fixed and in some embodiments the terminal hybridized nucleotide of the oligonucleotide probe is extendable for further ligation.

It is to be understood that according to some aspects, the nucleic acid origami structure need not be adjacent and/or attached to the terminal hybridized nucleotide in the oligonucleotide probe. The nucleic acid origami structure may be attached to the oligonucleotide probe by a linker molecule. Exemplary embodiments include the nucleic acid origami structure adjacent and/or attached to one of the nucleotides within the oligonucleotide probe such that detection of the detectable moiety confirms hybridization and/or ligation of a particular oligonucleotide probe from within the set and the identity of the hybridized nucleotide of the oligonucleotide probe to which the nucleic acid origami structure is attached, as a particular nucleic acid origami structure may be associated with a known particular A, C, G, or T of the hybridized nucleotide to which the template-nonhybridizing nucleic acid structure is attached.

According to a further exemplary embodiment, the nucleic acid origami structure need not be adjacent and/or attached to the nucleotide it will identify. For example, the nucleic acid origami structure may be adjacent and/or attached to the terminal hybridized nucleotide, but the nucleic acid origami structure or detectable moiety or barcode attached thereto is indicative of a known A, C, G or T at a known position within the hybridized and/or ligated oligonucleotide probe. According to this aspect, the oligonucleotide probe is designed with a particular nucleic acid origami structure indicative of a particular nucleotide at a particular position along the oligonucleotide probe. Also, the oligonucleotide probe is designed with a particular nucleic acid origami structure indicative of a subset or all of the nucleotides in the oligonucleotide probe.

As an exemplary aspect, a set of oligonucleotide probes having N nucleotides is prepared including a nucleic acid origami structure adjacent and/or attached to one of the N nucleotides and indicative of one of the N nucleotides at a particular position within the oligonucleotide probe, indicative of a plurality of nucleotides at particular positions within the oligonucleotide probe or indicative of all of the nucleotides in the oligonucleotide probe. The nucleic acid origami structure may be a unique nucleic acid origami structure or it may include one or more detectable moieties or barcodes uniquely identifying the desired nucleotides in the oligonucleotide probe. According to this aspect, a desired nucleotide anywhere within the oligonucleotide probe or plurality of desired nucleotides within the probe or the entire sequence of the oligonucleotide probe may be identified for a given cycle of hybridization/and or ligation and identification and/or detection of the nucleic acid origami structure.

The nucleic acid origami structure may include one or more probe hybridization sites for hybridizing with a probe including a detectable moiety with each probe hybridization site corresponding to a nucleotide in the oligonucleotide probe. For example, the oligonucleotide probe may include a nucleic acid origami structure with a probe hybridization site corresponding to the known terminal hybridized nucleotide in the oligonucleotide probe. Hybridizing a probe with a detectable moiety to the probe hybridization site on the nucleic acid origami structure and detecting the detectable moiety identifies the terminal hybridized nucleotide, and the corresponding complementary nucleotide in the template nucleic acid.

The nucleic acid origami structure may include a plurality of probe hybridization sites with each probe hybridization site corresponding to a particular nucleotide at a particular position in the oligonucleotide probe. According to this aspect, for an oligonucleotide of N nucleotides, the nucleic acid origami structure may have N probe hybridization sites, with each probe hybridization site corresponding to a specific nucleotide at a specific location along the oligonucleotide probe. According to an additional aspect, for an oligonucleotide of N nucleotides, the nucleic acid origami structure may have N or fewer probe hybridization sites, with each probe hybridization site corresponding to a specific nucleotide at a specific location along the oligonucleotide probe. According to this aspect, the oligonucleotide probe may include a nucleic acid origami structure having 1, 2, 3, 4, 5, or 6, etc., or up to N probe hybridization sites such that the oligonucleotide probe can be used to detect one nucleotide, N nucleotides or fewer than N nucleotides.

Embodiments of the present disclosure include the use of probes described herein for detecting and identifying a plurality of nucleotides, such as two nucleotides, more than two nucleotides, more than three nucleotides, more than 4 nucleotides, more than 5 nucleotides, more than 6 nucleotides, etc. in an oligonucleotide probe as a result of a single ligation step or cycle.

According to one aspect of the present disclosure, a nucleic acid origami structure is cleavably attached to the oligonucleotide probe. The nucleic acid origami structure has a cleavable nucleotide immediately attached to a terminal hybridized nucleotide of the oligonucleotide probe. The cleavable nucleotide may be part of a double stranded portion of the nucleic acid origami structure which is connected to a geometrically distinct or geometrically unique structure.

According to this aspect, such a combination promotes cleavage at the desired cleavage site leaving a precise oligonucleotide probe of known length thereby reducing bias. According to an additional aspect, an optional step is provided of removing the nucleic acid origami structure by cleavage of the cleavable nucleotide and generating an extendable terminus on the extended hybridized sequence. According to one aspect, the step of cleaving can generate an extendable terminus available for ligation. According to an alternate aspect, a nonextendable terminus of the oligonucleotide probe can be modified to be an extendable terminus available for ligation. According to this aspect, additional oligonucleotide probes can then repeatedly be hybridized and ligated in series along the single stranded nucleic acid template wherein after each ligation, one or more or all of the nucleotides of the hybridized and ligated oligonucleotide probe are identified and one or more or all of the complementary nucleotides in the template nucleic acid are identified.

In order to sequence each nucleotide in the nucleic acid template, the ligation and/or hybridization methods described herein may be repeated along the length of the nucleic acid template and then the methods repeated one or more nucleotides out of phase along the length of the nucleic acid template compared to the sequencing method previously performed. In this manner, where a single nucleotide is identified using an oligonucleotide primer of N nucleotides (as an example), ligation and/or hybridization is repeated N−1 times one nucleotide out of phase. Stated differently, the starting nucleotide in each successive sequencing method is out of phase by one nucleotide thereby allowing the identification of successive nucleotides of the template nucleic acid.

According to an additional aspect of the methods of the present disclosure, a dual probe is provided that includes a first oligonucleotide probe, a nucleic acid origami structure and a second oligonucleotide probe. According to one aspect, the nucleic acid origami structure is intermediate the first oligonucleotide probe and the second oligonucleotide probe such that the first oligonucleotide probe and the second oligonucleotide probe may hybridize to the nucleic acid template with the nucleic acid origami structure therebetween.

A sequencing primer is hybridized to a nucleic acid template. The first oligonucleotide probe and the second oligonucleotide probe of the dual probe each hybridize to the single stranded nucleic acid template with the first oligonucleotide probe being ligated to the sequencing primer to form an extended hybridized sequence. According to one aspect, the nucleic acid origami structure is used to identify one or more or all of the nucleotides in one or both of the first oligonucleotide probe or the second oligonucleotide probe.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 2 is a schematic depicting hybridization and ligation of two oligonucleotide probes to a DNA template with each oligonucleotide probe having a geometrically similar nucleic acid structure but with each having a set of detectable moieties acting as a barcode for a known probe sequence.

FIG. 3 is a schematic representation of 3D barrel shaped geometrically distinct or spatially distinct nucleic acid structure, i.e. DNA origami structure, barcoded with fluorescent particles.

FIG. 8A: Green channel (CY3), FIG. 8B: Red channel (CY5), FIG. 8C: superposition of both channels.

DETAILED DESCRIPTION

Figure 1:
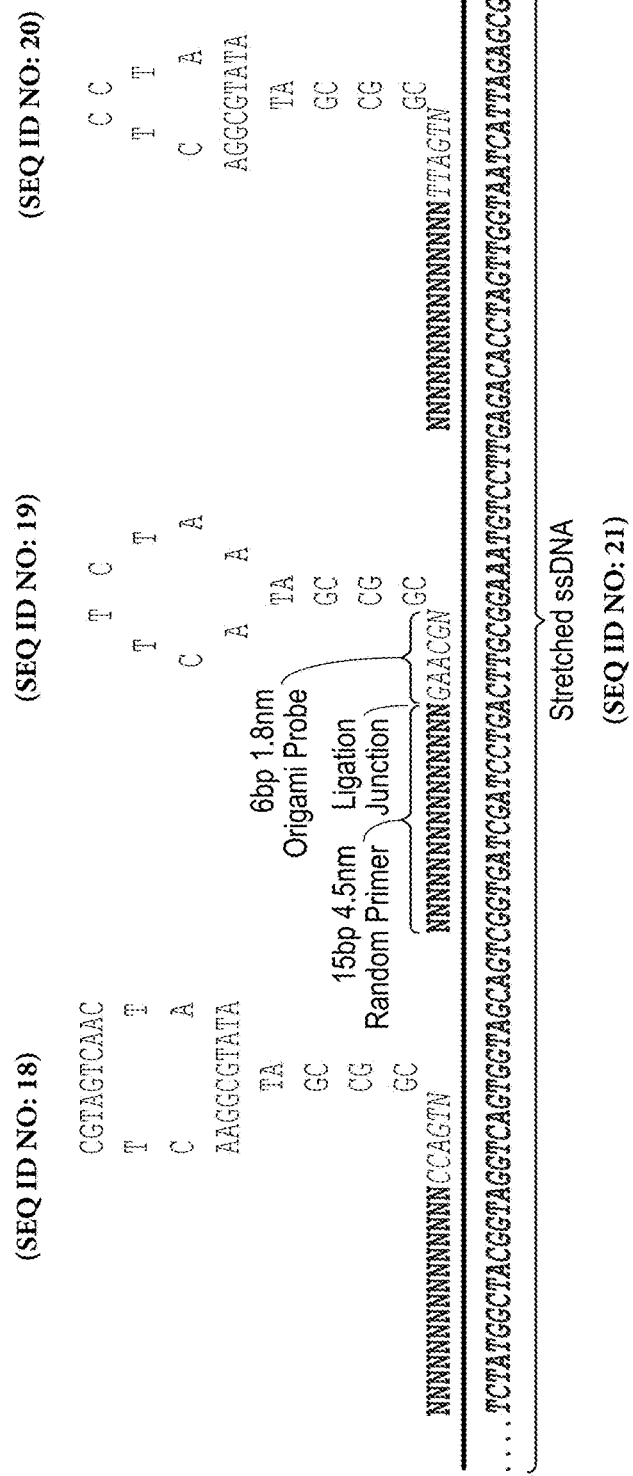
FIG. 1 is a schematic depicting hybridization and ligation of three oligonucleotide probes to a DNA template with each oligonucleotide probe having a geometrically distinct nucleic acid structure representative of a known probe sequence.

The principles of the present invention may be applied with particular advantage to determine the identity of oligonucleotide sequences. Terms and symbols of nucleic acid chemistry, biochemistry, genetics, and molecular biology used herein follow those of standard treatises and texts in the field, e.g., Komberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

Aspects of the present disclosure include the use of nucleic acid origami structures in sequencing procedures. Nucleic acid origami structures, also referred to as DNA origami structures or DNA origami, are two dimensional or three dimensional arbitrary shapes formed from nucleic acids. The DNA origami may be non-naturally occurring nucleic acid nanostructures of arbitrary two dimensional or three dimensional shape. In general, a non-naturally occurring nucleic acid nanostructure of arbitrary two dimensional or three dimensional shape can be made by folding a single stranded nucleic acid scaffold into a custom shape and using oligonucleotide strands to hybridize with the folded single stranded nucleic acid scaffold and hold it into a custom shape. The structure of a DNA origami may be any arbitrary structure as desired. The DNA origami may be attached to an oligonucleotide probe and used as a unique identifier of one or more or all of the nucleotides in the probe to which the DNA origami is attached. According to one aspect, a unique DNA origami structure is attached to each oligonucleotide probe in a set of probes used in sequencing methods. The sequence of each oligonucleotide probe in the set is known and accordingly, the unique DNA origami structure is associated with a known oligonucleotide probe sequence.

According to one aspect, the DNA origami structure is spatially distinct. According to one aspect, the DNA origami structure is geometrically distinct. According to one aspect, the DNA origami structure can be directly visualized using methods known to those of skill in the art. According to one aspect, DNA origami may take the form of any desired shape whether two dimensional or three dimensional. A unique DNA origami structure may be associated with a known oligonucleotide probe sequence. Accordingly, a set of oligonucleotide probes of known sequence with each having a known unique DNA origami structure associate with each known sequence is provided. Therefore, according to certain aspects of the disclosure, a unique DNA origami structure may be used as a barcode for a particular oligonucleotide probe sequence. During a sequencing method, a unique DNA origami structure may be identified and accordingly, the probe sequence to which it is attached can also be identified. Since DNA origami can serve as a unique identifier or barcode, the DNA origami attached to an oligonucleotide sequence can identify, as desired, any one or plurality or all of the nucleotides of the probe to which it is attached.

FIG. 1 depicts aspects of certain embodiments of the methods and probes described herein. According to FIG. 1, a nucleic acid template is provided. The nucleic acid template may include a single stranded nucleic acid template, such as a single stranded DNA template which may be stretched as indicated by the stretched ssDNA in FIG. 1. As shown in FIG. 1, one or more sequencing primers is hybridized to a sequencing primer hybridization site. The sequencing primers are spaced apart a distance along the single stranded DNA template. Sequencing primers may be between about 10 and about 20 nucleotides in length. The sequencing primers may be random primers as shown in FIG. 1 by the sequence (SEQ ID NO:1) NNNNNNNNNNNNNNN. However, the sequencing primers may be semi-random primers. The sequencing primers may be non-random to the extent that sequencing primers are designed to hybridize with certain desired locations on the single stranded DNA template. According to one aspect, a set of sequencing primers is contacted to the single stranded DNA template and sequencing primers hybridize at various locations along the length of the single stranded DNA template. The sequencing primers can be designed such that there is a desired length of DNA between each hybridized sequencing primer.

With reference to any particular sequencing primer hybridization site, adjacent to the sequencing primer hybridization site on the nucleic acid template is a first template nucleotide NTI followed by template nucleotides NT2 to NT6. As shown in FIG. 1, oligonucleotide probe referred to as an "origami probe" is hybridized to the nucleic acid template and includes 6 nucleotides which hybridize respectively to the 6 corresponding template nucleotides NT1 to NT6. The nucleotide of the origami probe adjacent to the terminal nucleotide of the sequencing primer is ligated to the terminal nucleotide of the sequencing primer. Methods and materials for sequencing by ligation are known to those of skill in the art and include those described in Shendure et al., Accurate Multiplex Polony Sequencing of an Evolved Bacterial Genome, *Science*, vol. 309, p. 1728-32 (2005) hereby incorporated by reference in its entirety. Connected to the origami probe is a nucleic acid origami structure ("DNAOM") which is spatially distinct or geometrically distinct, an example of which is shown as a two dimensional circular structure. According to one aspect, the spatially distinct or geometrically distinct nucleic acid structure is representative of a known probe sequence. Other nucleic acid origami structures are shown as a two dimensional square and a two dimensional triangle. The nucleic acid origami structures include a double stranded nucleic acid stem. The double stranded stem is connected to nucleotide N6 of the oligonucleotide or "origami" probe. According to one aspect, the double stranded stem is connected to nucleotide N6 of the oligonucleotide probe by a cleavable nucleotide. The cleavable nucleotide may also be referred to as a cut site or cleaving site as the cleavable nucleotide is removed from the oligonucleotide probe. According to certain aspects, the nucleic acid origami structure may be attached to the probe by a spacer molecule or tether molecule or an extender molecule which is understood herein to be a molecule capable of being attached to both the probe and the nucleic acid origami structure and which distances the nucleic acid origami structure from the probe. Such molecules can be double stranded nucleic acids, carbon chains and other molecules known to those of skill in the art useful as spacer molecules or tether molecules. Exemplary molecules useful as spacers, tethers, or extenders and the like include single stranded homopolymer nucleic acid sequences (such as between about 20 and about 45 nucleotides, between about 25 and about 40 nucleotides or such as about 36 nucleotides), alkyl chain extenders for example of between about 10 and about 30 carbon atoms (such as between about 15 and about 25 carbon atoms, such as about 18 carbon atoms), polyethylene glycol chains, tetrahydrofuran derivatives and the like. Exemplary single stranded homopolymer nucleic acid sequences include a chain or sequence of 36 dTTP nucleotides.

As shown in FIG. 1, each geometrically distinct nucleic acid origami structure is representative of the known nucleotides in the probe to which it is attached. For example, the circular origami structure is representative of the nucleic acid sequence GAACG in the probe GAACGN. The square origami structure is representative of the nucleic acid sequence CCAGT in the probe CCAGTN. The triangle origami structure is representative of the nucleic acid sequence TTAGT in the probe TTAGTN. It is to be understood that FIG. 1 is merely an illustration of aspects of the present disclosure and is not meant to be limiting in any way. According to certain aspects, a unique DNA origami structure can be created for any known nucleic acid sequence in a probe.

For a set of probes with all combinations of 5 known nucleotides in sequence, $4^5$ or 1024 probes can be created with each probe having a unique DNA origami structure corresponding to the known 5 base sequence. Accordingly, 1024 unique DNA origami structures are created. Each unique DNA origami structure is assigned to a specific known nucleotide probe sequence and is attached to the specific known nucleotide probe sequence. This technique can be used with any probe length and any known nucleic acid sequence length within a probe.

The structure of the unique DNA origami is visually recognizable and therefore distinguishable from other unique DNA origami shapes. Methods of making unique DNA origami shapes of arbitrary design or desired design are described in Rothemund, "Folding DNA to Create Nanoscale Shapes and Patterns", *Nature* March 2006, p. 297-302, vol. 440; Rothemund, "Design of DNA Origami", Proceedings of the International Conference of Computer-Aided Design (ICCAD) 2005; and U.S. Pat. No. 7,842,793 each of which are hereby incorporated by reference in its entirety.

According to an additional embodiment, a DNA origami structure may include one or more detectable moieties at one or more locations within or on the DNA origami structure. One or more detectable moieties can act as a barcode for a particular probe sequence. One or more detectable moieties at one or more locations within or on the DNA origami can act as a barcode for a particular probe sequence. According to one aspect, the visually detectable spatial orientation of the DNA origami or the one or more detectable moieties at one or more locations within or on the DNA origami, or both, can act as a barcode for a particular probe sequence. According to an exemplary embodiment, DNA origami may encoded with features specific to a particular nucleic acid probe sequence. Additionally, DNA origami may be tagged with metal nano-particles or fluorophores to enhance distinguishability when analyzed or imaged. Additionally, DNA origami may be tagged with metal nano-particles or fluorophores at distinct locations to enhance distinguishability when analyzed or imaged.

As shown in FIG. 1, the single stranded nucleic acid template is stretched, straight or partially straight. Methods of stretching or straightening nucleic acids are known to those of skill in the art and include Chung et al., Biomimetic Self-templating Supramolecular Structures, *Nature* 478, p. 364-368 (2011); Bensimon et al., Stretching DNA with a Receding Meniscus: Experiments and Models, *Physical Review Letters*, v74 n23, p. 4754-4757 (1995); and Zimmermann et al., DNA stretching on Functionalized Gold Surfaces, *Nucleic Acids Research*, v22 n3, p. 492-497 (1994) each of which are hereby incorporated by reference in their entireties.

According to one aspect, the single stranded DNA template can be straightened or partially straightened. According to one aspect, the single stranded DNA template can be straightened or partially straightened prior to hybridization with sequencing primers and/or probes. According to one aspect, the single stranded DNA template can be straightened or partially straightened after hybridization with sequencing primers and/or probes.

According to one aspect, the single stranded DNA template can be straightened or partially straightened using shear flow with the single stranded DNA template in buffer solution. Shear flow can be created by flowing fluid through a channel as with a flowcell or through the drying of a meniscus. In addition, DNA can be straightened or partially straightened by attaching the DNA to a needle and pulling the DNA as described in WO2009/046445, paragraph 147 and FIGS. 7, 8 and 15 hereby incorporated by reference herein. According to one aspect, the single stranded DNA template is straightened on a substrate that can aid in imaging, such as a copper EM grid, a glass slide, or silicon wafer. The substrates should be treated to allow the single stranded DNA template to be attached to the surface of the substrate, such as by aminosilane treatment in the case of a glass or silicon substrate or glow discharge as is the case with an EM grid. Also, prior to straightening, a single end of the single stranded DNA template (either 5' or 3' end) may be functionalized and attached to the substrate to allow more accurate positional control of the straightened DNA. Additional methods of attaching DNA to substrates are known to those of skill in the art.

According to one aspect, straightening or partially straightening the nucleic acid template facilitates detection of the DNA origami as the two dimensional DNA origami or the three dimensional DNA origami structure can be more easily distinguished from the straight or partially straight nucleic acid template. According to a certain aspect, the DNA origami can include larger and more visually recognizable distinct features thereby providing a size gain or a magnetic gain through field distortion.

According to one aspect, a scanning instrument can be used to visualize and distinguish nucleic acid origami structures. In an exemplary embodiment, the scanning instrument is an electron microscope. Exemplary electron microscopes include a transmission electron microscope (TEM), a scanning electron microscope (SEM), a scanning transmission electron microscope (STEM), and environmental scanning electron microscope (ESEM), a cryo-electron microscope (cryo-EM) and other electron microscopes known to those of skill in the art which can be used to identify local DNA conformation. Transmission electron microscopes and methods of using TEMs are known to those of skill in the art. See Morel, "Visualization of Nucleic Acids," *The Spreading of Nucleic Acids*, p. 35-56, CRC Press, Boca Raton (1995) hereby incorporated by reference in its entirety. According to one aspect, the nucleic acid template and the hybridized oligonucleotide probes with the DNA origami motifs are visible to the nanometer scale. The EM scanning system scans along the length of the linear or straight or partially straight construct of the nucleic acid template and the hybridized oligonucleotide probes with the DNA origami motifs. According to one aspect, image processing, edge detection, and object recognition algorithms (such as the Sobel algorithm) can be used to detect the end points and direction vector of the nucleic acid template, and inform the motion of the stage. The construct of the nucleic acid template and the hybridized oligonucleotide probes with the DNA origami motifs are stained with heavy metal for EM imaging.

According to additional aspects, the construct of the nucleic acid template and the hybridized oligonucleotide probes with the DNA origami motifs may be analyzed by methods known to those of skill in the art including high spatial resolution microscopy or super resolution microscopy such as stochastic optical reconstruction microscopy (STORM). Other stochastic methods include spectral precision distance microscopy (SPDM), photoactivated localization microscopy (PALM). Additional methods include deterministic methods such as stimulated emission depletion (STED), ground state depletion (GSD) and spatially structured illumination microscopy (SSIM). Still additional methods include scanning probe microscopy such as atomic force microscopy or scanning tunneling microscopy (STM), as well as, magnetic particles and a magnetic pickup, similar to a hard disk drive head.

FIG. 2 depicts an aspect of FIG. 1 where the nucleic acid origami structures attached to the probes are similar or of the same structure. According to the embodiment of FIG. 2, each DNA origami structure includes one or more detectable moieties which uniquely distinguish each DNA origami structure. As shown in FIG. 2, the DNA origami structures differ in a detectable label so that the two DNA origami structures can be distinguished. According to one aspect, a DNA origami structure can act as a scaffold for the attachment of one or more detectable moieties or barcodes such that the DNA origami construct can serve as a barcode for the probe to which it is attached. According to this aspect, unique DNA origami constructs can be created for each unique probe in a probe set. For example, for a 5 base probe sequence, $4^5$ or 1024 unique DNA origami constructs can be prepared to uniquely barcode each probe sequence within the set of 1024 probes.

FIG. 3 depicts a fluorescent barcoded DNA origami structure. As can be seen, different detectable moieties (fluorophores) can be attached to different locations on the DNA origami structure to create a unique DNA origami construct.

Figure 4A:
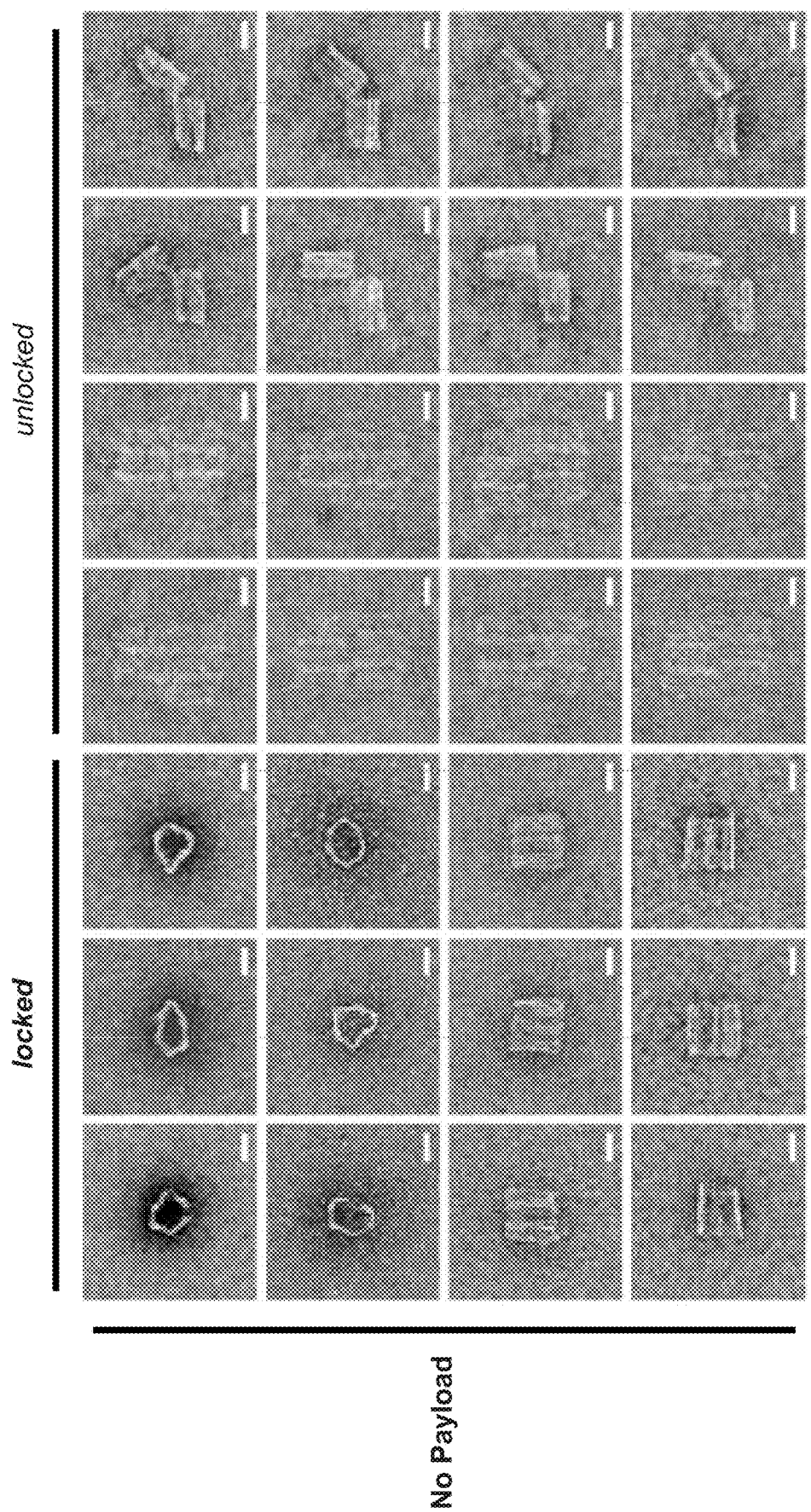
FIGS. 4A-4C are a series of TEM images of geometrically distinct three dimensional nucleic acid origami structures and shapes, with and without detectable gold nanoparticle probes (scale bar 20 nm).
Figure 4B:
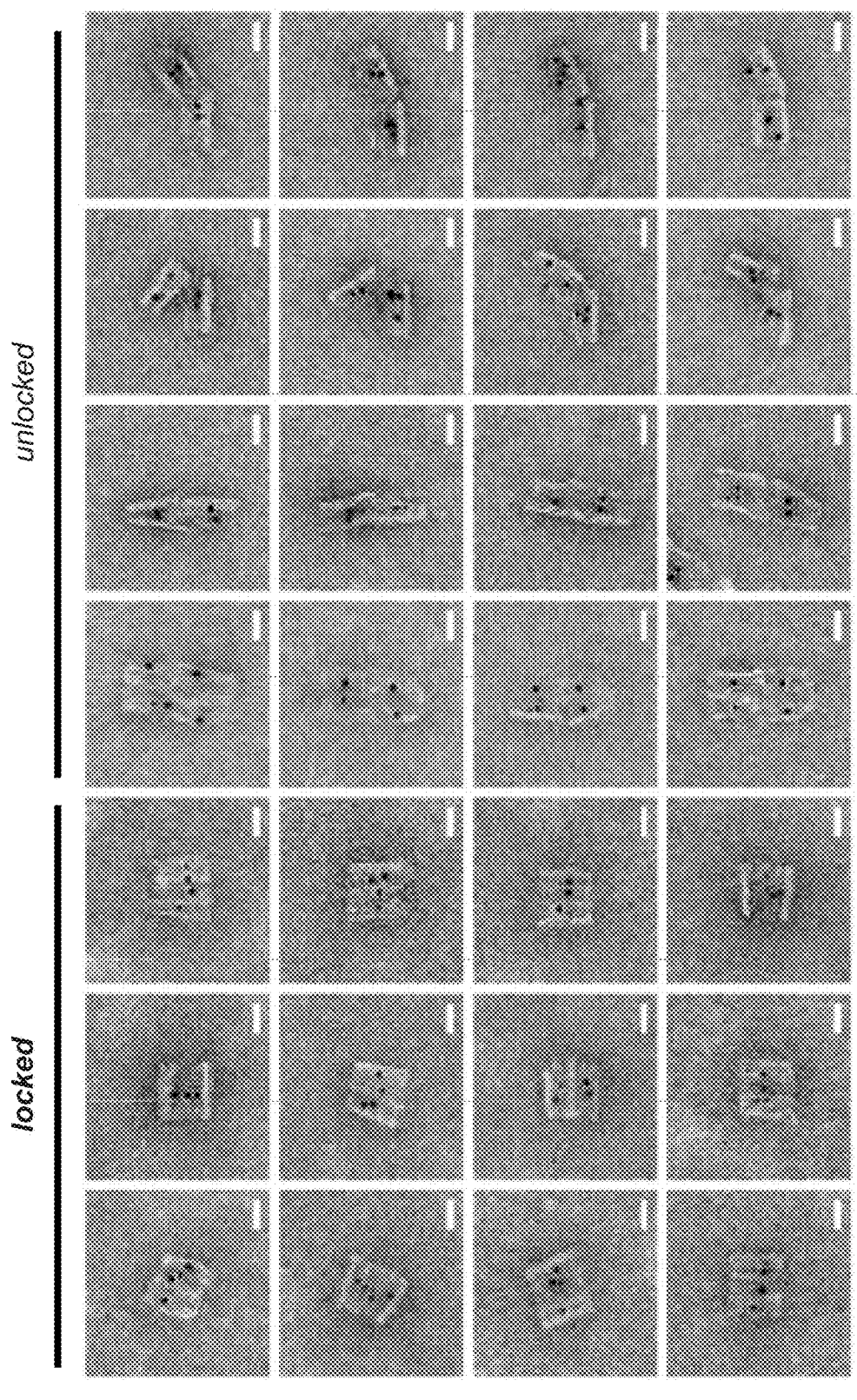
Figure 4C:
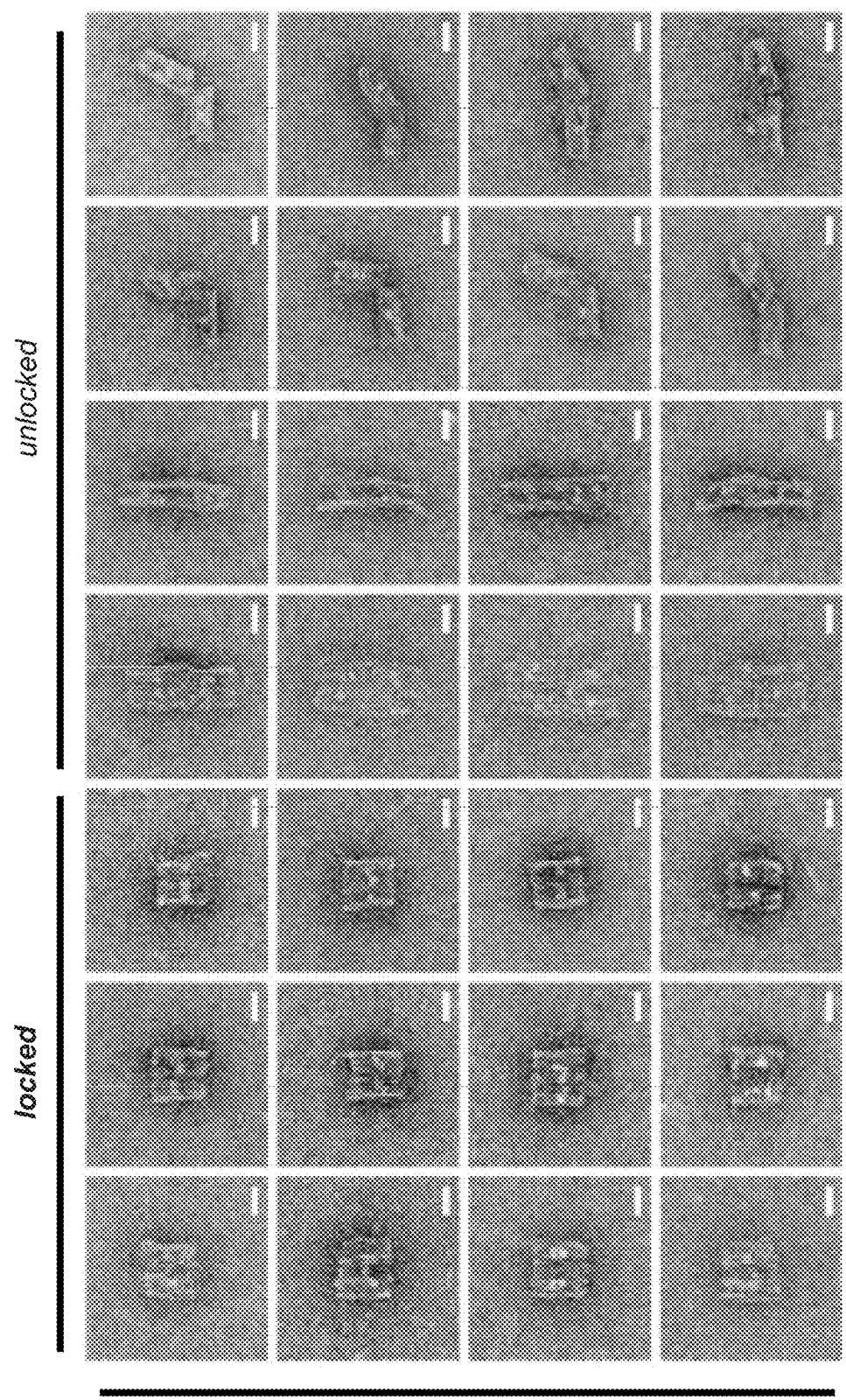

FIGS. 4A-4C depict different DNA origami shapes useful in the present disclosure. Some of the DNA origami structures are tagged with gold probes at various locations on the DNA origami shapes. Some of the DNA origami structures are tagged with antibody fragments at various locations on the DNA origami shapes.

Target Polynucleotides

Target polynucleotides, also referred to as oligonucleotides or template oligonucleotides, to be sequenced according to the methods described herein can be prepared in a variety of ways known to those of skill in the art. According to one aspect, target polynucleotides are single stranded nucleic acids. The length of the target polynucleotide can vary. According to certain aspects, the length of the target polynucleotide can be between about 1 nucleotide to about 3,000,000 nucleotides in length, between about 1 nucleotide to about 2,500,000 nucleotides in length, between about 1 nucleotide to about 2,000,000 nucleotides in length, between about 1 nucleotide to about 1,500,000 nucleotides in length, between about 1 nucleotide to about 1,000,000 nucleotides in length, between about 1 nucleotide to about 500,000 nucleotides in length, between about 1 nucleotide to about 250,000 nucleotides in length, between about 1 nucleotide to about 200,000 nucleotides in length or between about 1 nucleotide to about 150,000 nucleotides in length. Exemplary target polynucleotide can be between about 1 nucleotide to about 100,000 nucleotides in length, between about 1 nucleotide to about 10,000 nucleotides in length, between about 1 nucleotide to about 5,000 nucleotides in length, between about 4 nucleotides to about 2,000 nucleotides in length, between about 6 nucleotides to about 2,000 nucleotides in length, between about 10 nucleotides to about 1,000 nucleotides in length, between about 20 nucleotides to about 100 nucleotides in length, and any range or value in between whether overlapping or not.

A template for sequencing can be prepared from several linear or circular sources of polynucleotides, such as dsDNA, ssDNA, cDNA, RNA and synthesized or naturally occurring oligonucleotides.

An exemplary template is a synthesized oligonucleotide of the form (SEQ ID NO:2) 5'-PO$_4$-GTT CCT CAT TCT CTG AAG ANN NNN NNN NNN NNN NNN NNN NNN NNN NNN NNN NNN NAC TTC AGC TGC CCC GG-3'-OH, where the N portion represents a ssDNA template to be identified, (SEQ ID NO:3) GTT CCT CAT TCT CTG AAG A and (SEQ ID NO:4) AC TTC AGC TGC CCC GG represent adapters that will be used as a sequencing primer hybridization site (PS1). According to aspects of the present disclosure, sequencing can be accomplished in either the 5' to 3' direction or the 3' to 5' direction or both directions simultaneously. According to certain aspects, multiple copies of the template nucleic acid are prepared using methods known to those of skill in the art. According to one aspect, the ssDNA template can be circularized using ssDNA Circligase II (Epicentre # CL9025K) or other ssDNA ligase such as Circligase I (Epicentre # CL4115K), or by template-directed ligation using a combination of a dsDNA ligase (e.g. (T3, T4, T7 and other ds DNA ligases) with a bridge oligo (SEQ ID NO:5) (5'-ATGAGGAACCCGGGGCAG-3'-PO$_4$). Chemical ligation methods have also been described (Dolinnaya et al., 1993; Kumar et al., 2007).

According to one aspect, 10 pmol of ssDNA template is circularized using Circligase II, according to the manufacturer's recommendation. Following the circularization, 20 units of Exonuclease I (Enzymatics # X801L) and 100 units of Exonuclease III (Enzymatics # X802L) are added to the reaction to digest any remaining linear template. Next, rolling circle amplification (RCA) is performed on the circular ssDNA template using a DNA polymerase with high processivity, strong displacement activity and low error rate. Rolling circle amplification methods are known to those of skill in the art and include Drmanac et al., Human genome sequencing using unchained base reads on self-assembling DNA nanoarrays, *Science*, vol. 327, p. 78-81 (2009). According to one aspect, 1 pmol of the circularized template is used with 20 units of phi29 DNA polymerase (Enzymatics # P702L). Additionally, dNTP (typically 1 mM) and a RCA primer (typically 1 pmol) are required. An exemplary RCA primer would have the form (SEQ ID NO:6) 5'-AATGAGGAACCCGGGGCA*G*C, where the * represents a phosphorothioate bond thereby indicating that the last 3' nucleotide bears a phosphorothioate bond, making the RCA less susceptible to phi29 3'→5' exonuclease activity. However, an exemplary RCA primer may not include such phosphorothioate bonds, especially if the polymerase used does not have 3'→5' exonuclease activity. Alternatively, an exemplary RCA primer may have phosphorothioate bonds on the 5' side of the RCA primer such as (SEQ ID NO:7) 5'-A*A*TGAGGAACCCGGGGCAGC. An annealing reaction is often performed before adding the phi29 (95° C. for 1 min, then 2 min cool down to 4° C.), to increase the RCA efficiency. Then the reaction is incubated at 30° C. for an hour (incubation periods between 15 min to 6 hours may also be used). Other temperatures can be used, since phi29 is active between 4° C. and 40° C. (with 90% diminished activity). Then, the reaction is cooled to 4° C. and the RCA products (referred to as Rolony) are recovered in cold PBS and can be stored at 4° C. until needed. Rolling circle amplification products prepared this way are stable for several months and can be used as template for assaying sequencing techniques.

A template can also be prepared using dsDNA from a biological source. The genomic DNA would first be extracted using one of the several extraction kits commercially available for that purpose. Then, the dsDNA would be fragmented to any length or a specific length, using a mechanical (Covaris focused electroacoustic, Nebulizer, sonication, vortex) or enzymatic (e.g. Fragmentase) fragmentation. While, it may be practical to keep the fragments size between 100 and 1000 nucleotides, any size can be used. For example, the length of the target polynucleotide template can be between about 1 nucleotide to about 3,000,000 nucleotides in length, between about 1 nucleotide to about 2,500,000 nucleotides in length, between about 1 nucleotide to about 2,000,000 nucleotides in length, between about 1 nucleotide to about 1,500,000 nucleotides in length, between about 1 nucleotide to about 1,000,000 nucleotides in length, between about 1 nucleotide to about 500,000 nucleotides in length, between about 1 nucleotide to about 250,000 nucleotides in length, between about 1 nucleotide to about 200,000 nucleotides in length or between about 1 nucleotide to about 150,000 nucleotides in length. Exemplary target polynucleotide templates can be between about 1 nucleotide to about 100,000 nucleotides in length, between about 1 nucleotide to about 10,000 nucleotides in length, between about 1 nucleotide to about 5,000 nucleotides in length, between about 4 nucleotides to about 2,000 nucleotides in length, between about 6 nucleotides to about 2,000 nucleotides in length, between about 10 nucleotides to about 1,000 nucleotides in length, between about 20 nucleotides to about 100 nucleotides in length, and any range or value in between whether overlapping or not. In certain instances, the target polynucleotide may be an entire strand of genomic DNA or a portion or fragment thereof.

The ends of the fragmented dsDNA are repaired and phosphorylated in one step using a mix of T4 DNA polymerase and T4 Polynucleotide Kinase (Enzymatics # Y914-HC-L), according to the manufacturer instructions. Other DNA polymerase with 3'→5' exonuclease activity and low or no strand displacement activity can be used. Adapters composed of dsDNA oligonucleotides are added to the dsDNA using a DNA ligase, typically T3 (Enzymatics # L601L) or T4 DNA ligase (Enzymatics # L603-HC-L). The reaction is performed at room temperature for 20 min according to the manufacturer instructions. The adapters can be in the form Ad1 (SEQ ID NO:8) 5'-GTTCCTCAT-TCTCTGAAGA, Ad2 (SEQ ID NO:9) 5'-TCTTCAGA-GAATGAG, Ad3 (SEQ ID NO:10) 5'-CCGGGGCAGCT-GAAGT, and Ad4 (SEQ ID NO:11) 5'-ACTTCAGCTGCC, where Ad1-Ad2 are annealed together and Ad3-Ad4 anneal together, before being ligated. After ligation, the 5' overhang ends are filled-in using a DNA polymerase with, such as Bst DNA polymerase large fragment (NEB # M0275L). Next, limited PCR (typically 6 to 8 cycles) is performed to generate multiple copies using PCR primer in the form (SEQ ID NO:12) 5'-PO$_4$-GTTCCTCATTCTCTGAAGA and (SEQ ID NO:13) 5'-Biotin-CCGGGGCAGCTGAAGT. The 5'biotin is then attached to one end of the dsDNA to streptavidin coated magnetic beads (Invitrogen #65305), allowing the other end to be recovered by performing the Circligase II reaction, as described above, with the exception that the template is attached to the beads. This is performed by incubating the reaction at 65° C. for 2 h, which will allow the DNA strand with 5'-PO$_4$ to be de-anneal and be circularized. After exonuclease digest, the circular ssDNA template is now ready for rolling circle amplification (RCA) as discussed above. Adapters can also be in the form Ad5 (SEQ ID NO:14) 5'-GAAGTCTTCTTACTCCTTGGGC- CCCGTCAGACTTC and Ad6 (SEQ ID NO:15) 5'-GTTC-CGAGATTTCCTCCGTTGTTGTTAATCGGAAC, where Ad5 and Ad6 each form hairpin structures to be ligated on each side of the dsDNA, virtually creating a circular ssDNA product ready for RCA. A pull down assay can be used to select templates bearing one of each hairpin and not two of the same. In this case, an oligonucleotide complementary to one loop in the form (SEQ ID NO:16) 5'-Biotin-TAACAACAACGGAGGAAA-C3sp will be bound to streptavidin coated magnetic beads. Next RCA can be performed using a RCA primer (SEQ ID NO:17) (5'-ACGGGGCCCAAGGAGTA*A*G), as described above.

Other amplification methods can be used. In general, "amplifying" includes the production of copies of a nucleic acid molecule of the array or a nucleic acid molecule bound to a bead via repeated rounds of primed enzymatic synthesis. "In situ" amplification indicated that the amplification takes place with the template nucleic acid molecule positioned on a support or a bead, rather than in solution. In situ amplification methods are described in U.S. Pat. No. 6,432,360.

Varied choices of polymerases exist with different properties, such as temperature, strand displacement, and proofreading. Amplification can be isothermal, as described above and in similar adaptation such as multiple displacement amplification (MDA) described by Dean et al., Comprehensive human genome amplification using multiple displacement amplification, *Proc. Natl. Acad. Sci. U.S.A.*, vol. 99, p. 5261-5266. 2002; also Dean et al., Rapid amplification of plasmid and phage DNA using phi29 DNA polymerase and multiply-primed rolling circle amplification, *Genome Res.*, vol. 11, p. 1095-1099. 2001; also Aviel-Ronen et al., Large fragment Bst DNA polymerase for whole genome amplification of DNA formalin-fixed paraffin-embedded tissues, *BMC Genomics*, vol. 7, p. 312. 2006. Amplification can also cycle through different temperature regiments, such as the traditional polymerase chain reaction (PCR) popularized by Mullis et al., Specific enzymatic amplification of DNA in vitro: The polymerase chain reaction. *Cold Spring Harbor Symp. Quant. Biol.*, vole 51, p. 263-273. 1986. Variations more applicable to genome amplification are described by Zhang et al., Whole genome amplification from a single cell: implications for genetic analysis, *Proc. Natl. Acad. Sci. U.S.A.*, vol. 89, p. 5847-5851. 1992; and Telenius et al., Degenerate oligonucleotide-primed PCR: general amplification of target DNA by a single degenerate primer, *Genomics*, vol. 13, p. 718-725. 1992. Other methods include Polony PCR described by Mitra and Church, In situ localized amplification and contact replication of many individual DNA molecules, *Nuc. Acid. Res.*, vole 27, pages e34. 1999; emulsion PCR (ePCR) described by Shendure et al., Accurate multiplex polony sequencing of an evolved bacterial genome, *Science*, vol. 309, p. 1728-32. 2005; and Williams et al., Amplification of complex gene libraries by emulsion PCR, *Nat. Methods*, vol. 3, p. 545-550. 2006. Any amplification method can be combined with a reverse transcription step, a priori, to allow amplification of RNA. According to certain aspects, amplification is not absolutely required since probes, reporters and detection systems with sufficient sensitivity can be used to allow detection of a single molecule using template non-hybridizing nucleic acid structures described. Ways to adapt sensitivity in a system include choices of excitation sources (e.g. illumination) and detection (e.g. photodetector, photomultipliers). Ways to adapt signal level include probes allowing stacking of reporters, and high intensity reporters (e.g. quantum dots) can also be used.

Amplification methods useful in the present disclosure may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification.

In certain exemplary embodiments, methods for amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach* and *PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 68-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 µL. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

In general, target polynucleotides, template nucleotides, template non-hybridizing nucleic acids or probes described herein include the terms "nucleic acid molecule," "nucleic acid sequence," "nucleic acid fragment," "oligonucleotide" and "polynucleotide" and are used interchangeably and are intended to include, but not limited to, a polymeric form of nucleotides that may have various lengths, either deoxyribonucleotides or ribonucleotides, or analogs thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Oligonucleotides useful in the methods described herein may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Oligonucleotide sequences may be isolated from natural sources or purchased from commercial sources. In certain exemplary embodiments, oligonucleotide sequences may be prepared using one or more of the phosphoramidite linkers and/or sequencing by ligation methods known to those of skill in the art. Oligonucleotide sequences may also be prepared by any suitable method, e.g., standard phosphoramidite methods such as those described herein below as well as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; *Synthetic DNA Arrays* In Genetic Engineering, Vol. 20:111, Plenum Press (1998); Duggan et al. (1999) *Nat. Genet.* S21:10; *Microarrays: Making Them and Using Them* In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

Solid Phase Supports

In certain exemplary embodiments, one or more template nucleic acid sequences, i.e. oligonucleotide sequences, described herein are immobilized on a support (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. When using a support that is substantially planar, the support may be physically separated into regions, for example, with trenches, grooves, wells, or chemical barriers (e.g., hydrophobic coatings, etc.).

In certain exemplary embodiments, a support is a microarray. As used herein, the term "microarray" refers in one embodiment to a type of assay that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate creates a substantially planar surface. Spatially defined sites may additionally be "addressable" in that its location and the identity of the immobilized probe at that location are known or determinable.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, probes are immobilized via one or more of the cleavable linkers described herein. The density of non-overlapping regions containing nucleic acids in a microarray is typically greater than 100 per $cm^2$, and more typically, greater than 1000 per $cm^2$. Microarray technology relating to nucleic acid probes is reviewed in the following exemplary references: Schena, Editor, *Microarrays: A Practical Approach* (IRL Press, Oxford, 2000); Southern, *Current Opin. Chem. Biol.*, 2: 404-410 (1998); *Nature Genetics* Supplement, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861; nitrocellulose: Ranki et al. (1983) *Gene* 21:77; cellulose: Goldkorn (1986) *Nucleic Acids Res.* 14:9171; polystyrene: Ruth et al. (1987) Conference of Therapeutic and Diagnostic Applications of Synthetic Nucleic Acids, Cambridge U.K.; teflon-acrylamide: Duncan et al. (1988) *Anal. Biochem.* 169:104; polypropylene: Polsky-Cynkin et al. (1985) *Clin. Chem.* 31:1438; nylon: Van Ness et al. (1991) *Nucleic Acids Res.* 19:3345; agarose: Polsky-Cynkin et al., *Clin. Chem.* (1985) 31:1438; and sephacryl: Langdale et al. (1985) *Gene* 36:201; latex: Wolf et al. (1987) *Nucleic Acids Res.* 15:2911).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

Sequencing Primers

Sequencing primers according to the present disclosure are those that are capable of binding to a known binding region of the target polynucleotide and facilitating ligation of an oligonucleotide probe of the present disclosure. Sequencing primers may be designed with the aid of a computer program such as, for example, DNAWorks, or Gene2Oligo. The binding region can vary in length but it should be long enough to hybridize the sequencing primer. Target polynucleotides may have multiple different binding regions thereby allowing different sections of the target polynucleotide to be sequenced. Sequencing primers are selected to form highly stable duplexes so that they remain hybridized during successive cycles of ligation. Sequencing primers can be selected such that ligation can proceed in either the 5' to 3' direction or the 3' to 5' direction or both. Sequencing primers may contain modified nucleotides or bonds to enhance their hybridization efficiency, or improve their stability, or prevent extension from a one terminus or the other.

According to one aspect, single stranded DNA templates (ssDNA) are prepared by RCA as described above to be used with sequencing primers. Alternatively single stranded template is attached to beads or nanoparticles in an emulsion and amplified through ePCR. The result is clonal beads with a single amplified ssDNA template.

For the purpose of identifying several template nucleotide sequences in parallel, the templates are diluted in PBS buffer pH 7.4, and either bound to a patterned or non-patterned substrate utilizing various attachment methods, such as Biotin-Strepavidin, azide-alkyle (e.g. click chemistry), NHS-ester or Silanization (e.g. aldehyde-, epoxy-, amino-silane). According to one aspect, rolonies are attached to a patterned surface, such as a $SiO_2$ solid surface, treated with 1% aminosilane (v/v) and let to interact for a period of time (typically between 5 minutes to 2 hours). Any unbound templates are then washed away using Wash 1 buffer.

Next, a sequencing primer is prepared and hybridized to the sequencing primer hybridizing site. According to certain aspects, sequencing primers can be prepared which can hybridize to a known sequence of the template. Alternatively, during template preparation, adapters with a known nucleic acid sequence are added to the unknown nucleic acid sequence by way of ligation, amplification, transposition or recombination according to methods known to those of skill in the art and described herein. Still alternatively, sequencing primers having a certain level of degeneracy could be used to hybridize to certain positions along the template. According to one aspect, primer degeneracy is used to allow primers to hybridize semi-randomly along the template. Primer degeneracy is selected based on statistical methods known to those of skill in the art to facilitate primers hybridizing at certain intervals along the length of the template. According to this aspect, primers can be designed having a certain degeneracy which facilitates binding every N bases, such as every 100 bases, every 200 bases, every 2000 bases, every 100,000 bases. The binding of the primers along the length of the template is based on the design of the primers and the statistical likelihood that a primer design will bind about every N bases along the length of the template. Since the sequencing primer P1 will be extended by ligation, the terminal group of the sequencing primer is typically synthesized to be ready to be covalently joined to the oligonucleotide probe by the DNA ligase. If the ligation occurs between the 5' end of the sequencing primer and the 3' end of the oligonucleotide probe, a phosphate group (5'-$PO_4$) must be present on the sequencing primer while a hydroxyl group (3'-OH) on the oligonucleotide probe, and vice-versa. To hybridize the sequencing primer to the sequencing primer hybridizing site, 1 uM of the sequencing primer diluted in 5×SSPE buffer is used. The mixture is then incubated for a few minutes above room temperature to encourage proper annealing (typically between 1 to 5 minutes, at temperature between 25 and 55° C.).

Oligonucleotide Probes

Oligonucleotide probes according to the present disclosure are those having between about 1 nucleotide to about 100 nucleotides. Exemplary oligonucleotide probes include between about 1 nucleotide to about 20 nucleotides, between about 3 nucleotides to about 15 nucleotides, between about 5 nucleotides to about 12 nucleotides or between about 6 nucleotides to about 10 nucleotides. An exemplary oligonucleotide probe includes about 6 nucleotides. According to one aspect, oligonucleotide probes according to the present disclosure should be capable of hybridizing to the single stranded nucleic acid template. According to an additional aspect, oligonucleotide probes according to the present disclosure may be capable of hybridizing to the single stranded nucleic acid template and ligating to a sequencing primer or an extended duplex to generate the extended duplex for the next ligation cycle. According to a still additional aspect, a combination of oligonucleotide probes can be used where a first probe is capable of hybridizing to the single stranded nucleic acid template and ligating to a sequencing primer or an extended duplex to generate the extended duplex for the next ligation cycle and a second probe is capable of hybridizing to the single stranded nucleic acid template. Probes according to the present disclosure may include a nucleic acid origami structure. Oligonucleotide probes may be designed with the aid of a computer program such as, for example, DNAWorks, or Gene2Oligo.

Oligonucleotide probes according to the present disclosure may include a terminal moiety which prevents multiple ligations in a single ligation cycle. Oligonucleotide probes according to the present disclosure should also be capable of being modified to create or include an extendable terminus for further ligation if an extendable terminus is not already present. Oligonucleotide probes according to the present disclosure need not form a perfectly matched duplex with the single stranded nucleic acid template, though a perfect matched duplex is exemplary. Instead, oligonucleotide probes need only have a perfect match between a nucleotide in the probe and the complementary nucleotide being identified by the methods described herein.

Hybridization and Ligation of Oligonucleotide Probes

Methods of hybridizing and ligating oligonucleotide probes to a single stranded template nucleic acid are known to those of skill in the art. "Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual*, 2nd Ed. Cold Spring Harbor Press (1989) and Anderson *Nucleic Acid Hybridization*, $1^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

Ligation can be accomplished either enzymatically or chemically. "Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references: Whitely et al., U.S. Pat. No. 4,883,750; Letsinger et al., U.S. Pat. No. 5,476,930; Fung et al., U.S. Pat. No.

5,593,826; Kool, U.S. Pat. No. 5,426,180; Landegren et al., U.S. Pat. No. 5,871,921; Xu and Kool (1999) *Nucl. Acids Res.* 27:875; Higgins et al., *Meth. in Enzymol.* (1979) 68:50; Engler et al. (1982) *The Enzymes,* 15:3 (1982); and Namsaraev, U.S. Patent Pub. 2004/0110213.

Chemical ligation methods are disclosed in Ferris et al., Nucleosides & Nucleotides, 8: 407-414 (1989) and Shabarova et al., Nucleic Acids research, 19: 4247-4251 (1991). Enzymatic ligation utilizes a ligase. Many ligases are known to those of skill in the art as referenced in Lehman, Science, 186: 790-797 (1974); Engler et al., DNA ligases, pages 3-30 in Boyer, editor, The Enzymes, Vol. 15B (Academic Press, New York, 1982); and the like. Exemplary ligases include T4 DNA ligase, T7 DNA ligase, *E. coli* DNA ligase, Taq ligase, Pfu ligase and the like. Certain protocols for using ligases are disclosed by the manufacturer and also in Sambrook, Molecular Cloning: A Laboratory manual, $2^{nd}$ Edition (Cold Spring Harbor Laboratory, New York, 1989); barany, PCR Methods and Applications, 1:5-16 (1991); Marsh et al., Strategies, 5:73-76 (1992).

If ligation is not 100% efficient, it may be desirable to cap extended duplexes that fail to undergo ligation so that they do not participate in further ligation steps. According to certain aspects, capping can be done by removing the 5'phosphate (5'PO) using an alkaline phosphatase. By example, following ligation of the oligonucleotide probes for sequencing, unreacted 5'PO are removed by adding an alkaline phosphatase in solution, such as 10 units of calf insetting alkaline phosphatase (NEB # M0393L) in 100 µL of its reaction buffer. The reaction is incubated for 15 minutes at room temperature. Other alkaline phosphatases are suitable. Capping can also be done by using a polymerase, deficient in exonuclease activity, to add a terminal nucleotide in the 5'→3' direction (so capping the 3' end of a primer). Terminal nucleotide varies but most frequently used are dideoxynucleotides (ddNTP) and acyclonucleotides (acyNTP). A nontemplated nucleotide can also be used as a terminal nucleotide. Capping by polymerase extension is performed as described to amplify a polynucleotide sequence using DNA polymerases, except that dNTP normally used in the reaction are substituted by terminal NTP (e.g. ddNTP), which prevent the DNA polymerase or Terminal Transferase (TdT) of adding more than one nucleotide. By example, following ligation of the oligonucleotide probes for sequencing, a capping mix is added, which consists of 1 mM of ddNTP and 20 units of Terminal Transferase (NEB # M0315L) in 100 µL of its reaction buffer. The reaction is incubated for 15 minutes at room temperature. Alternatively, capping can be done by ligating an oligonucleotide, ideally between 6-9mer long, with a capped end. The cap can be in the form of 5'hydroxyl (5'OH), instead of 5'PO, and oppositely 3'PO instead of 3'OH, a terminal NTP (ddNTP, inverted ddNTP, acyNTP) or an oligo with a terminal carbon spacer (e.g. C3 spacer). This method would work as well for capping the 5'end or the 3'end of the polynucleotyde sequence to be capped. Capping by ligation is performed as described for ligating an oligonucleotide probe. By example, following ligation of the oligonucleotide probes for sequencing, a capping mix is added, which consists of 1 uM of a 5'- or 3'-capped oligonucleotide added to the ligation buffer with 1200 units of T4 DNA ligase, per 100 µL reaction volume. The reaction is incubated for 15 minutes at room temperature.

According to the present disclosure, a specific set of oligonucleotide probes L1 is utilized to hybridize to the ssDNA template and covalently linked to the sequencing primer P1 by a DNA ligase. Oligonucleotide probes L1 are prepared in ligation buffer (typically at 1 uM), and ligated using 6000 units of T3 DNA ligase (Enzymatics # L601L) or 1200 units of T4 DNA ligase (Enzymatics # L603-HC-L) per 100 µL reaction volume. The reaction is allowed to incubate at room temperature for a few minutes to several hours (typically between 5 minutes to 2 hours, at a temperature between 15° C. and 35° C.). Then the enzymes and any unligated oligonucleotide probes L1 are washed away with wash 1 buffer.

Hybridization Conditions

In certain exemplary embodiments, the terms "annealing" and "hybridization," as used herein, are used interchangeably to mean the formation of a stable duplex. In one aspect, stable duplex means that a duplex structure is not destroyed by a stringent wash under conditions such as a temperature of either about 5° C. below or about 5° C. above the $T_m$ of a strand of the duplex and low monovalent salt concentration, e.g., less than 0.2 M, or less than 0.1 M or salt concentrations known to those of skill in the art. The term "perfectly matched," when used in reference to a duplex means that the polynucleotide and/or oligonucleotide strands making up the duplex form a double stranded structure with one another such that every nucleotide in each strand undergoes Watson-Crick base pairing with a nucleotide in the other strand. The term "duplex" includes, but is not limited to, the pairing of nucleoside analogs, such as deoxyinosine, nucleosides with 2-aminopurine bases, PNAs, and the like, that may be employed. A "mismatch" in a duplex between two oligonucleotides means that a pair of nucleotides in the duplex fails to undergo Watson-Crick bonding.

As used herein, the term "hybridization conditions," will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, e.g., conditions under which a probe will specifically hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* $1^{st}$ Ed., BIOS Scientific Publishers Limited (1999). As used herein, the terms "hybridizing specifically to" or "specifically hybridizing to" or similar terms refer to the binding, duplexing, or hybridizing of a molecule substantially to a particular nucleotide sequence or sequences under stringent conditions.

Nucleic Acid Origami Structures

According to certain aspects of the present disclosure, a nucleic acid origami structure is a two dimensional structure or a three dimensional structure which is created from DNA. The terms spatially distinct nucleic acid structure, geometrically distinct nucleic acid structure, spatially resolvable nucleic acid structure, spatially observable nucleic acid structure are intended to include the term DNA origami. DNA origami may be a megadalton-scale DNA nanostructure created from one or more or a plurality of DNA strands. According to an exemplary aspect, a nucleic acid origami structure is created from a scaffold strand of a nucleic acid, such as DNA, which is arranged into a desired macromolecular object of a custom shape. Staples strands of DNA, which may be shorter than the scaffold strand of DNA, can be used to direct the folding or other orientation of the scaffold strand of DNA into a programmed arrangement. The term "origami" infers that one or more strands or building blocks of DNA may be folded or otherwise positioned into a desired structure or shape. The desired structure or shape which may then be secured into a desired shape or structure by one or more other strands or building blocks of DNA, such as a plurality of staple strands of DNA. Methods of making DNA origami are known to those of skill in the art. Representative methods include Rothemund, "Folding DNA to Create Nanoscale Shapes and Patterns", *Nature* March 2006, p. 297-302, vol. 440; Rothemund, "Design of DNA Origami", Proceedings of the International Conference of Computer-Aided Design (ICCAD) 2005; U.S. Pat. No. 7,842,793; Douglas et al., *Nuc. Acids Res.*, vol. 37, no. 15, pp. 5001-5006; and Douglas et al., *Nature,* 459, pp. 414-418 (2009); Andersen et al., *Nature,* 459, pp. 73-76 (2009); Deitz et al., Science, 325, pp. 725-730 (2009); Han et al., Science, 332, pp. 342-346 (2011); Liu et al., Angew. Chem. Int. Ed., 50, pp. 264-267 (2011); Zhao et al., Nano Lett., 11, pp. 2997-3002 (2011); Woo et al., Nat. Chem. 3, pp. 620-627 (2011) Torring et al., Chem. Soc. Rev. 40, pp. 5636-5646 (2011) each of which are hereby incorporated by reference in their entireties. According to an exemplary aspect, a nucleic acid origami structure need not be constructed of a scaffold strand and staple strands. A nucleic acid origami structure can be constructed by single stranded nucleic acid sequences which self-assemble into tiles to form lattices of any desired shape or size. Such single stranded nucleic acid sequences may be de novo designed and synthesized. Such approaches include programmed self-assembly of such designed strands of nucleic acids to create a wide range of structures with desired shapes. See Wei et al., Nature, volume 485, pp. 623-627 (2012) hereby incorporated by reference in its entirety.

It is to be understood that the principles of the present disclosure do not rely on any particular method of making DNA origami or any particular two dimensional or three dimensional nucleic acid shape. It is to be understood that aspects of the ability of DNA origami to provide unique shapes is useful to barcode or otherwise identify specific nucleic acids or nucleic acid sequences. It is to be further understood that aspects of the ability to design DNA origami with desired hybridization sites or desired probes is useful to barcode or otherwise identify specific nucleic acids or nucleic acid sequences. It is to be further understood that the ability of DNA origami to be of sufficient size to be identified by visualizing the shape of the DNA origami is useful to barcode or otherwise identify specific nucleic acids or nucleic acid sequences. It is to be further understood that the ability of DNA origami to be of sufficient size to be directly visually distinguishable is useful to barcode or otherwise identify specific nucleic acids or nucleic acid sequences. It is to be further understood that the ability of DNA origami to be megadalton-scale nucleic acid (such as DNA) nanostructures of sufficient size to be identified by visualizing the shape of the DNA origami is useful to barcode or otherwise identify specific nucleic acids or nucleic acid sequences. According to certain aspects, the DNA origami are visually distinguishable or identifiable without the aid of fluorescent detectable moieties. According to certain aspects, a set of DNA origami are provided which are each distinct based on the shape of the DNA origami or the presence and/or position of detectable moieties on the DNA origami. According to certain aspects, a set of DNA origami barcodes are provided which are used to uniquely identify a nucleic acid or nucleic acid sequence such as a nucleic acid probe.

According to certain aspects of the present disclosure, a nucleic acid origami structure is attached to an oligonucleotide probe. The nucleic acid origami structure may include a detectable moiety, label, reporter and/or barcode. The nucleic acid origami structure may include a probe hybridization site for hybridizing with a probe having a detectable moiety, label, reporter or barcode. The nucleic acid origami structure may have a geometrically distinct or geometrically unique structure.

Methods of making nucleic acid origami structures are known to those of skill in the art. Methods of attaching a detectable moiety, label or reporter to a nucleic acid sequence are known to those of skill in the art.

Detectable Moieties

In certain exemplary embodiments, a detectable moiety, label or reporter can be used to detect one or more nucleotides described herein. Oligonucleotides described herein can be labeled in a variety of ways, including the direct or indirect attachment of a detectable moiety such as a fluorescent moiety, colorimetric moiety and the like. One of skill in the art can consult references directed to labeling DNA. Examples of detectable moieties include various radioactive moieties, enzymes, prosthetic groups, fluorescent markers, luminescent markers, bioluminescent markers, metal particles, protein-protein binding pairs, protein-antibody binding pairs and the like. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, phycoerythrin and the like. Examples of bioluminescent markers include, but are not limited to, luciferase (e.g., bacterial, firefly, click beetle and the like), luciferin, acquorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}$I, $^{35}$S, $^{14}$C, or $^{3}$H. Identifiable markers are commercially available from a variety of sources.

Fluorescent labels and their attachment to nucleotides and/or oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); and Wetmur, *Critical Reviews in Biochemistry and Molecular Biology,* 26:227-259 (1991). Particular methodologies applicable to the invention are disclosed in the following sample of references: U.S. Pat.

Nos. 4,757,141, 5,151,507 and 5,091,519. In one aspect, one or more fluorescent dyes are used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847, 162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labelling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY TM 630/650-14-dUTP, BODIPY TM 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY TM FL-14-UTP, BODIPY TMR-14-UTP, BODIPY TM TR-14-UTP, RHODAMINE GREEN™-5-UTP, ALEXA FLUOR™ 488-5-UTP, LEXA FLUOR™ 546-14-UTP (Molecular Probes, Inc. Eugene, Oreg.) and the like. Alternatively, the above fluorophores and those mentioned herein may be added during oligonucleotide synthesis using for example phosphoroamidite or NHS chemistry. Protocols are known in the art for custom synthesis of nucleotides having other fluorophores (See, Henegariu et al. (2000) *Nature Biotechnol.* 18:345). 2-Aminopurine is a fluorescent base that can be incorporated directly in the oligonucleotide sequence during its synthesis. Nucleic acid could also be stained, a priori, with an intercalating dye such as DAPI, YOYO-1, ethidium bromide, cyanine dyes (e.g. SYBR Green) and the like.

Other fluorophores available for post-synthetic attachment include, but are not limited to, ALEXA FLUOR™ 350, ALEXA FLUOR™ 405, ALEXA FLUOR™ 430, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, Pacific Orange, rhodamine 6G, rhodamine green, rhodamine red, tetramethyl rhodamine, Texas Red (available from Molecular Probes, Inc., Eugene, Oreg.), Cy2, Cy3, Cy3.5, Cy5, Cy5.5, Cy7 (Amersham Biosciences, Piscataway, N.J.) and the like. FRET tandem fluorophores may also be used, including, but not limited to, PerCP-Cy5.5, PE-Cy5, PE-Cy5.5, PE-Cy7, PE-Texas Red, APC-Cy7, PE-Alexa dyes (610, 647, 680), APC-Alexa dyes and the like.

Metallic silver or gold particles may be used to enhance signal from fluorescently labeled nucleotide and/or oligonucleotide sequences (Lakowicz et al. (2003) *BioTechniques* 34:62).

Biotin, or a derivative thereof, may also be used as a label on a nucleotide and/or an oligonucleotide sequence, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP or aminohexylacrylamide-dCTP residue may be incorporated into an oligonucleotide sequence and subsequently coupled to an N-hydroxy succinimide (NHS) derivatized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels for an oligonucleotide sequence may include fluorescein (FAM, FITC), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for detection, in which each of the antibodies is derivatized with a detectable label: biotin/α-biotin, digoxigenin/a-digoxigenin, dinitrophenol (DNP)/α-DNP, 5-Carboxyfluorescein (FAM)/α-FAM.

In certain exemplary embodiments, a nucleotide and/or an oligonucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, PCT publication WO 91/17160 and the like. Many different hapten-capture agent pairs are available for use. Exemplary haptens include, but are not limited to, biotin, des-biotin and other derivatives, dinitrophenol, dansyl, fluorescein, CY5, digoxigenin and the like. For biotin, a capture agent may be avidin, streptavidin, or antibodies. Antibodies may be used as capture agents for the other haptens (many dye-antibody pairs being commercially available, e.g., Molecular Probes, Eugene, Oreg.).

According to certain aspects, detectable moieties described herein are spectrally resolvable. "Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in *Flow Cytometry: Instrumentation and Data Analysis* (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

In certain embodiments, the detectable moieties can provide higher detectability when used with an electron microscope, compared with common nucleic acids. Moieties with higher detectability are often in the group of metals and organometals, such as mercuric acetate, platinum dimethyl-sulfoxide, several metal-bipyridyl complexes (e.g. osmium-bipy, ruthenium-bipy, platinum-bipy). While some of these moieties can readily stain nucleic acids specifically, linkers can also be used to attach these moieties to a nucleic acid. Such linkers added to nucleotides during synthesis are acrydite- and a thiol-modified entities, amine reactive groups, and azide and alkyne groups for performing click chemistry. Some nucleic acid analogs are also more detectable such as gamma-adenosine-thiotriphosphate, iodode-oxycytidine-triphosphate, and matellonucleosides in general (see Dale et al., Proc. Nat. Acad. Sci. USA, Vol. 70, No. 8, pp. 2238-2242 (1973)). The modified nucleotides are added during synthesis. Synthesis may refer by example to solid support synthesis of oligonucleotides. In this case, modified nucleic acids, which can be a nucleic acid analog, or a nucleic acid modified with a detectable moiety, or with an attachment chemistry linker, are added one after each other to the nucleic acid fragments being formed on the solid support, with synthesis by phosphoramidite being the most popular method. Synthesis may also refer to the process performed by a polymerase while it synthesizes the complementary strands of a nucleic acid template. Certain DNA polymerases are capable of using and incorporating nucleic acids analogs, or modified nucleic acids, either modified with a detectable moiety or an attachment chemistry linker to the complementary nucleic acid template.

Cleavable Moieties

According to certain aspects of the present disclosure, cleavable nucleotide moieties also referred to as cleavable linkages are used to separate an oligonucleotide probe from a nucleic acid origami structure. Cleavable moieties are known to those of skill in the art and include chemically scissile internucleosidic linkages which may be cleaved by treating them with chemicals or subjecting them to oxidizing or reducing environments. Such cleavable moieties include phosphorothioate, phosphorothiolate which can be cleaved by various metal ions such as solutions of silver nitrate. Such cleavable moieties include phosphoroamidate which can be cleaved in acidic conditions such as solutions including acetic acid. A suitable chemical that can cleave a linkage includes a chemical that can cleave a bridged-phosphorothioate linkage and can remove a phosphoramidite linker from a nucleotide and/or oligonucleotide, leaving a free phosphate group on the nucleotide and/or oligonucleotide at the cleavage site. Suitable chemicals include, but are not limited to $AgNO_3$, $AgCH_3COO$, $AgBrO_3$, $Ag_2SO_4$, or any compound that delivers $Ag^{2+}$, $HgCl_2$, $I_2$, $Br_2$, $I^-$, $Br^-$ and the like.

Cleavable moieties also include those that can be cleaved by nucleases known to those of skill in the art. Such nucleases include restriction endonucleases such as Type I, Type II, Type III and Type IV, endonucleases such as endonucleases I-VIII, ribonucleases and other nucleases such as enzymes with AP endonuclease activity, enzymes with AP lyase activity and enzymes with glycosylase activity such as uracil DNA glycosylase.

Cleavable moieties also include those capable of being cleaved by light of a certain wavelength. Such cleavable moieties are referred to as photolabile linkages and are disclosed in Olejnik et al., Photocleavable biotin derivatives: a versatile approach for the isolation of biomolecules, *Proc. Natl. Acad. Sci. U.S.A.*, vol. 92, p. 7590-7594 (1995). Such photocleavable linkers can be cleaved by UV illumination between wavelengths of about 275 to about 375 nm for a period of a few seconds to 30 minutes, such as about one minute. Exemplary wavelengths include between about 300 nm to about 350 nm.

Certain nucleotides, such as dGTP, dCTP and dTTP could also be reacted before being incorporated for use as a cleavable linkage, making them specifically sensitive to further cleavage by nucleases or chemicals. According to one aspect, one or multiple deoxyguanosines in a given template non-hybridizing nucleic acid can be oxidized to 8-oxo-deoxyguanosine by 2-nitropropane, before being added to the sequencing reaction, and subsequently cleaved using an 8-oxoguanine DNA glycosylase (e.g. Fpg, hOGG1). Similarly, deoxycytosines can be pre-reacted to form 5-hydroxycytosine, using bisulfite or nitrous acid, which can then be processed by certain DNA-glycosylase, such as hNEIL1. Other nucleotides which can be cleaved include uracil, deoxyuridine, inosine and deoxyinosine.

Additional embodiments include nucleotides that may be cleaved in a two step method such as by a first step that modifies the nucleotide making it more susceptible to cleavage and then a second step where the nucleotide is cleaved. Such systems include the USER system (commercially available from Enzymatics (# Y918L) or New England Biolabs (# M5505L) which is typically a combination of UDG and Endonuclease VIII, although other endonucleases could be used. Enzymes UDG and endonuclease are commercially available. In addition, modified nucleotides may be cleavable nucleotides where a feature of the nucleotide has been modified, such as a bond, so as to facilitate cleavage. Examples include an abasic base, an apyrimidic base, an apurinic base, phospohrothioate, phosphorothiolate and oxidized bases such as deoxyguanosines which can be oxidized to 8-oxo-deoxyguanosine.

Accordingly, internucleotide bonds may be cleaved by chemical, thermal, or light based cleavage. Exemplary chemically cleavable internucleotide linkages for use in the methods described herein include, for example, □-cyano ether, 5'-deoxy-5'-aminocarbamate, 3'deoxy-3'-aminocarbamate, urea, 2'cyano-3',5'-phosphodiester, 3-(S)-phosphorothioate, 5'-(S)-phosphorothioate, 3'-(N)-phosphoramidate, 5'-(N)-phosphoramidate, □-amino amide, vicinal diol, ribonucleoside insertion, 2'-amino-3',5'-phosphodiester, allylic sulfoxide, ester, silyl ether, dithioacetal, 5'-thio-furmal, □-hydroxy-methyl-phosphonic bisamide, acetal, 3'-thio-furmal, methylphosphonate and phosphotriester. Internucleoside silyl groups such as trialkylsilyl ether and dialkoxysilane are cleaved by treatment with fluoride ion. Base-cleavable sites include □-cyano ether, 5'-deoxy-5'-aminocarbamate, 3'-deoxy-3'-aminocarbamate, urea, 2'-cyano-3',5'-phosphodiester, 2'-amino-3',5'-phosphodiester, ester and ribose. Thio-containing internucleotide bonds such as 3'-(S)-phosphorothioate and 5'-(S)-phosphorothioate are cleaved by treatment with silver nitrate or mercuric chloride. Acid cleavable sites include 3'-(N)-phosphoramidate, 5'-(N)-phosphoramidate, dithioacetal, acetal and phosphonic bisamide. An □-aminoamide internucleoside bond is cleavable by treatment with isothiocyanate, and titanium may be used to cleave a 2'-amino-3',5'-phosphodiester-O-ortho-benzyl internucleoside bond. Vicinal diol linkages are cleavable by treatment with periodate. Thermally cleavable groups include allylic sulfoxide and cyclohexene while photo-labile linkages include nitrobenzylether and thymidine dimer. Methods synthesizing and cleaving nucleic acids containing chemically cleavable, thermally cleavable, and photo-labile groups are described for example, in U.S. Pat. No. 5,700,642.

Accordingly, internucleotide bonds may be cleaved using enzymatic cleavage. Nucleic acid sequences described herein may be designed to include a restriction endonuclease cleavage site. A nucleic acid may be contacted with a restriction endonuclease to result in cleavage. A wide variety of restriction endonucleases having specific binding and/or cleavage sites are commercially available, for example, from New England Biolabs (Ipswich, Mass.). In various embodiments, restriction endonucleases that produce 3' overhangs, 5' overhangs or blunt ends may be used. When using a restriction endonuclease that produces an overhang, an exonuclease (e.g., RecJ$_f$, Exonuclease I, Exonuclease T, S$_1$ nuclease, P$_1$ nuclease, mung bean nuclease, CEL I nuclease, etc.) may be used to produce blunt ends. In an exemplary embodiment, an orthogonal primer/primer binding site that contains a binding and/or cleavage site for a type IIS restriction endonuclease may be used to remove the temporary orthogonal primer binding site.

As used herein, the term "restriction endonuclease recognition site" is intended to include, but is not limited to, a particular nucleic acid sequence to which one or more restriction enzymes bind, resulting in cleavage of a DNA molecule either at the restriction endonuclease recognition sequence itself, or at a sequence distal to the restriction endonuclease recognition sequence. Restriction enzymes include, but are not limited to, type I enzymes, type II enzymes, type IIS enzymes, type III enzymes and type IV enzymes. The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts et al. (2005) *Nucl. Acids Res.* 33:D230, incorporated herein by reference in its entirety for all purposes).

In certain aspects, primers of the present invention include one or more restriction endonuclease recognition sites that enable type IIS enzymes to cleave the nucleic acid several base pairs 3' to the restriction endonuclease recognition sequence. As used herein, the term "type IIS" refers to a restriction enzyme that cuts at a site remote from its recognition sequence. Type IIS enzymes are known to cut at a distances from their recognition sites ranging from 0 to 20 base pairs. Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.). Information about the recognition sites, cut sites and conditions for digestion using type IIs endonucleases may be found, for example, on the Worldwide web at neb.com/ nebecomm/enzymefinderserach bytypeIIs.asp). Restriction endonuclease sequences and restriction enzymes are well known in the art and restriction enzymes are commercially available (New England Biolabs, Ipswich, Mass.).

According to certain aspects, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., *Ann. Rev. Biochem.* 67:99-134 (1998); U.S. Pat. Nos. 5,739,386, 5,700,642 and 5,830, 655; and U.S. Patent Publication Nos. 2003/0186226 and 2004/0106728).

The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

In one embodiment, cleavable sites contained within the modified oligonucleotide may include chemically cleavable groups, such as dialkoxysilane, 3'-(S)-phosphorothioate, 5'-(S)-phosphorothioate, 3'-(N)-phosphoramidate, 5'-(N)phosphoramidate, and ribose. Synthesis and cleavage conditions of chemically cleavable oligonucleotides are described in U.S. Pat. Nos. 5,700,642 and 5,830,655. For example, depending upon the choice of cleavable site to be introduced, either a functionalized nucleoside or a modified nucleoside dimer may be first prepared, and then selectively introduced into a growing oligonucleotide fragment during the course of oligonucleotide synthesis. Selective cleavage of the dialkoxysilane may be effected by treatment with fluoride ion. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide.

In another embodiment, a non-cleavable hydroxyl linker may be converted into a cleavable linker by coupling a special phosphoramidite to the hydroxyl group prior to the phosphoramidite or H-phosphonate oligonucleotide synthesis as described in U.S. Patent Application Publication No. 2003/0186226. The cleavage of the chemical phosphorylation agent at the completion of the oligonucleotide synthesis yields an oligonucleotide bearing a phosphate group at the 3' end. The 3'-phosphate end may be converted to a 3' hydroxyl end by a treatment with a chemical or an enzyme, such as alkaline phosphatase, which is routinely carried out by those skilled in the art.

In another embodiment, the cleavable linking moiety may be a TOPS (two oligonucleotides per synthesis) linker (see e.g., PCT publication WO 93/20092). For example, the TOPS phosphoramidite may be used to convert a non-cleavable hydroxyl group on the solid support to a cleavable linker. A preferred embodiment of TOPS reagents is the Universal TOPS™ phosphoramidite. Conditions for Universal TOPS™ phosphoramidite preparation, coupling and cleavage are detailed, for example, in Hardy et al. *Nucleic Acids Research* 22(15):2998-3004 (1994). The Universal TOPS™ phosphoramidite yields a cyclic 3' phosphate that may be removed under basic conditions, such as the extended ammonia and/or ammonia/methylamine treatment, resulting in the natural 3' hydroxy oligonucleotide.

In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide.

In another embodiment, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al., *J. Org. Chem.* 61:525-529 (1996), Kahl et al., *J. Org. Chem.* 64:507-510 (1999), Kahl et al., *J. Org. Chem.* 63:4870-4871 (1998), Greenberg et al., *J. Org. Chem.* 59:746-753 (1994), Holmes et al., *J. Org. Chem.* 62:2370-2380 (1997), and U.S. Pat. No. 5,739,386. Ortho-nitrobenzyl-based linkers, such as hydroxymethyl, hydroxyethyl, and Fmoc-aminoethyl carboxylic acid linkers, may also be obtained commercially.

Example I

Total human genomic DNA was extracted from a fibroblast cell culture originally from a human skin biopsy, following methods to extract million bases long DNA by Pulse-Field Gel Electrophoresis (PFGE) and described by Zhang et al., Nature Protocols, vol. 7, no. 3, pp. 467-478 (2012), Michalet et al., Science, vol. 277, 1518 (1997) or CHEF Genomic DNA Plug Kits (Bio-Rad).

Fibroblast cells were grown to confluence (~2×10$^6$ cells/ml) using standard conditions, i.e. using complete growth medium DMEM (Life Technologies) containing 10% Fetal Bovine Serum (FBS), in an incubator at 37° C. and 5% $CO_2$. Upon confluence, DMEM and FBS were removed by washing with cold Phosphate Buffered Saline solution (PBS), and 0.05% trypsin-EDTA-PBS solution was added to the culture and incubated for 5 min on ice. The trypsinization was stopped by washing using DMEM and 10% FBS. The fibroblasts were then collected by pipetting and spun down in a centrifuge at 1000 g for 5 min.

Fibroblasts were resuspended in PBS with 1% Low Melting Point Agarose (LMP) and 100 μl was poured into agarose plug molds. Once solidified, the agarose plugs were extracted from their molds and transferred into a 50 ml tube containing the 500 μl of lysis buffer per plug, i.e. 1 mg/ml Proteinase K (NEB) in 0.5M EDTA and 1% N-lauroylsarcosine, freshly prepared. The plugs were incubated for 16 h at 50° C. with gentle agitation. The plugs were then washed with 50 mM EDTA and stored in 50 mM EDTA at 4° C.

To recover the DNA, the agarose plug was first melted at 68° C. in 1× agarase buffer (NEB) for 10 minutes and then cooled down to 42° C. and incubated for 2 h at 42° C. with 1 unit of beta-agarase I (NEB) per 100 μl volume. The enzyme was then heat-denatured at 68° C. for 10 minutes. Megabases long double-stranded DNA fragments were ready for manipulation.

Example II

The megabase long DNA was diluted in 100 mM MES ph 5.5 (Sigma), which favors attachment of the DNA 5' termini to a silanated surface. A glass microscope cover slip or a piece of silicon was treated with 1% vinylsilane (Sigma) and then rinsed with distilled water before being attached by a clip to a combing device and then dipped in a reservoir containing 200 μl of diluted DNA in MES. The reservoir has the proper dimension to minimize the volume while allowing the cover slip to be completely dipped into the liquid in the reservoir. The combing device included a syringe pump (Tecan model #737472), with the clip attached to the pump vertical axis, and the vertical motion of the pump was adjusted via computer software, and typically set at 250 μm/s.

Figure 5:
FIG. 5 is an image of stretched DNA stained with YOYO-1, captured by fluorescent microscopy (blue channel) at 320× magnification.

The cover slip was pulled from the reservoir, at a constant speed, which resulted in combing of the DNA at the meniscus. Once the cover slip was completely pulled-out from the reservoir containing DNA, it was rinsed with 2×SSC (300 mM sodium chloride, 30 mM trisodium citrate, pH 7.0) and assembled into a flow cell by superposing a clean microscope glass slide with a gasket in between to allow liquid flowing from one extremity to the other. FIG. 5 is an image of stretched DNA stained with YOYO-1 using fluorescent microscopy (blue channel) at 320× magnification. As shown in FIG. 5, megabase long DNA was stretched using the method described in Example II. If hybridization and ligation are to be performed, then the flow cell/slide may be washed with a solution containing 100 μg/ml Bovine Serum Albumin (BSA, NEB) to block the remaining binding sites. For example, after stretching the DNA, the slide may be washed with SSC, then washed with BSA and then washed with SSC.

Example III

While dsDNA can easily be linearized and deposited on a surface by several methods including molecular combing, a single-stranded nucleic acid fragment is typically preferred for interrogation using hybridization or ligation.

In one embodiment, dsDNA is rendered single stranded with the single strand attached to the cover slip by contacting the cover slip assembled into the flow cell with a denaturing solution containing 0.1N sodium hydroxide, or 100% formamide or 100% DMSO. The cover slip was contacted several times with the denaturing solution. Since the 5' termini of each DNA strand is preferentially bound to the vinylsilane-coated cover slip, the complementary DNA strand was displaced by the parallel flow of the denaturant. The denaturant is removed by washing using 2×SSC.

In another embodiment, one strand of the dsDNA was randomly nicked using the property of DnaseI to only partially digest the strand in the absence of manganese or magnesium ions. Briefly, 1 unit of DnaseI (NEB) was added to 100 μl of a 10 mM Tris-HCL pH 7.5 solution, and incubated and loaded in the flow cell containing the linearized DNA and incubated for 10 minutes at RT. Then it was washed extensively with 10 mM Tris-EDTA. Then 1 unit of Mung Bean nuclease (NEB) in 100 μl 1× Mung Bean Nuclease Buffer (NEB) was loaded into the flow cell and incubated at room temperature for 1 minute then washed extensively with 10 mM Tris-EDTA. This method creates partially digested and overlapping ssDNA fragments with a 5'phosphate and 3'hydroxyl groups, which are compatible with DNA ligation.

Example IV

Figure 6:
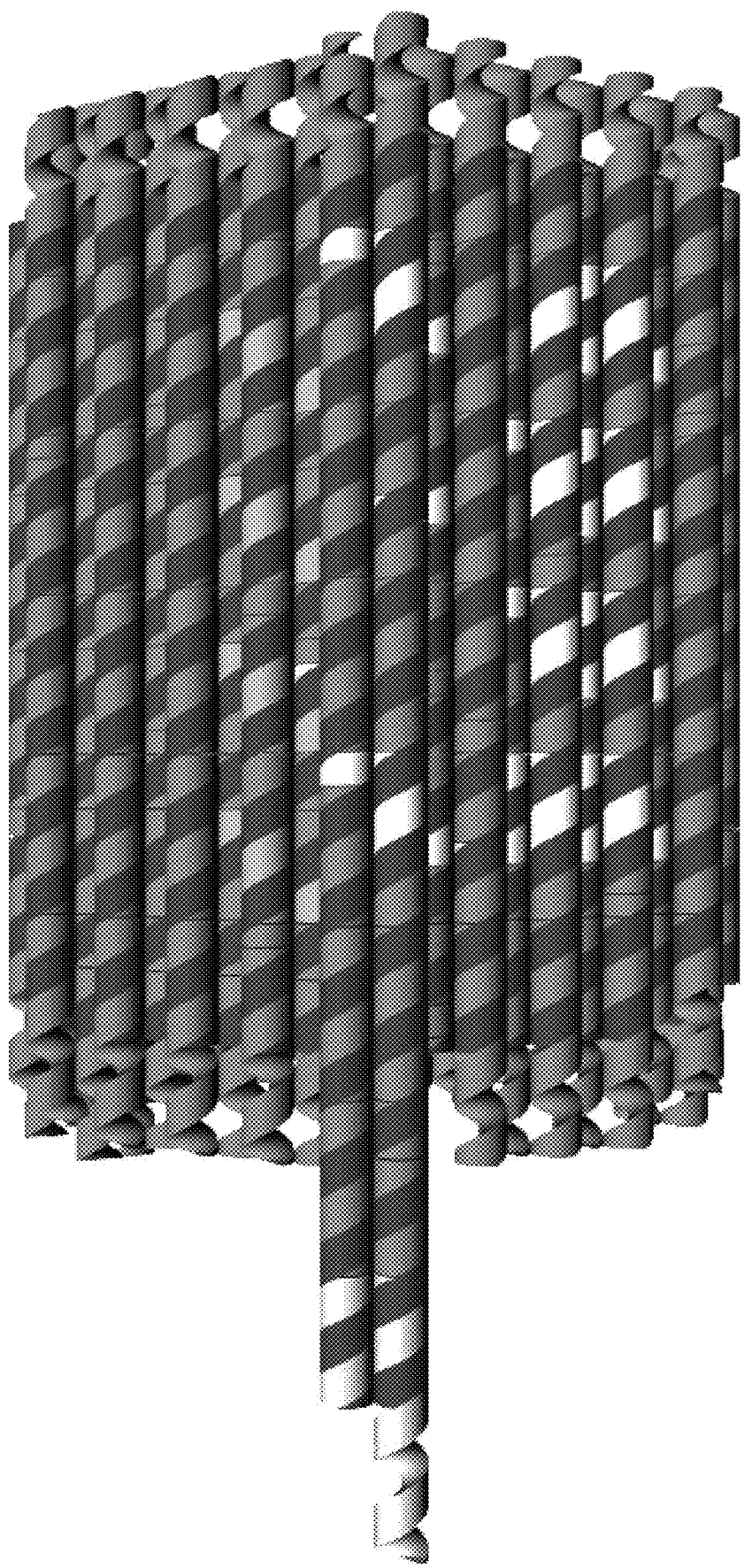
FIG. 6 is a 3D CAD representation of a barrel-shaped Origami, with a hanging ssDNA binding site (left side), designed using cadnano.

The DNA Origami structures were designed using the software cadnano2 (see cadnano.org; Douglas et al., *Nuc. Acids Res.*, vol. 37, no. 15, pp. 5001-5006 hereby incorporated by reference in its entirety). By example, a 100 nm long barrel shape can be designed, which also contains free ssDNA regions that will be used as binding sites to label the Origami with fluorescent oligo probe. FIG. 6 is a three dimensional CAD representation of a barrel-shaped DNA origami, with a hanging ssDNA binding site extending off of the barrel, which was designed using cadnano2. A list of oligo-staples were designed and submitted to IDT for synthesis.

The 3D origami structures where folded according to Douglas et al., *Nature*, 459(7245): 414-418. doi:10.1038/nature08016 (2009) incorporated by reference herein in its entirety. 100 nM of the staples were mixed with 20 nM of M13mp18, used as a scaffold DNA, in Origami folding buffer (5 mM Tris-EDTA with 16 mM Magnesium Chloride), in a 0.2 ml PCR tube. The DNA in the scaffold-staples was first denatured in a PCR machine at 95° C. for 10 seconds, then cooled down to 85° C. at a rate of 5° C. per 5 minutes, then to 70° C. at 1° C./5 min, then to 25° C. at 1° C./10 min. The reaction typically achieved above 95% folding efficiency. Removing the excess staples was done by filtering through an Amicon Ultra 100 kDa column (Millipore).

Following DNA origami folding, the DNA origami structures can be labeled with one of many DNA staining dyes, particles, nanoparticles, metals, or via fluorescently labeled oligonucleotide probes specific to each Origami (1 µl of 25 µM oligo-probe mix in 2×SSC). The Origami is filtered using an Amicon Ultra 100 kDa column (Millipore) using Origami folding buffer to equilibrate, wash and elute.

Example V

Labeled Origami probes were mixed in an equimolar ratio. 100 µL of ligation mix containing 1 µM of Origami-probe mix and 2000 U of T4 DNA ligase in 1×DNA Ligase buffer (Enzymatics) was loaded in the flow cell and incubated at room temperature for 30 min. The unligated Origami-probes were washed using 500 µL of 2×SSC.

Example VI

After hybridization, ligation and washes, the Origami bound to the template can be identified several ways. Fluorescently labeled Origami can be visualized using an epifluorescent microscope (e.g. Leica DM16000B) equipped with the appropriate objective (e.g. 20× PLAN APO), and filter sets (e.g. to detect Cy3, a filter block equipped with a 545/15 nm bandpass excitation filter, a 610/38 nm bandpass emission filter, and a 570 nm longpass dichromatic mirror is used). The fluorescent signal is indicative of the Origami sequence, which is then use to infer the template sequence.

Figure 7:
FIG. 7 is an image of Origami probes bound to an aminosilane-coated cover slip in the absence of template, captured by fluorescent microscopy at 320× magnification and blue, green and red channels superposed.

FIG. 7 is an image of Origami probes bound to an aminosilane-coated cover slip in the absence of template, captured by fluorescent microscopy at 320× magnification and blue, green and red channels superposed.

Figure 8A:
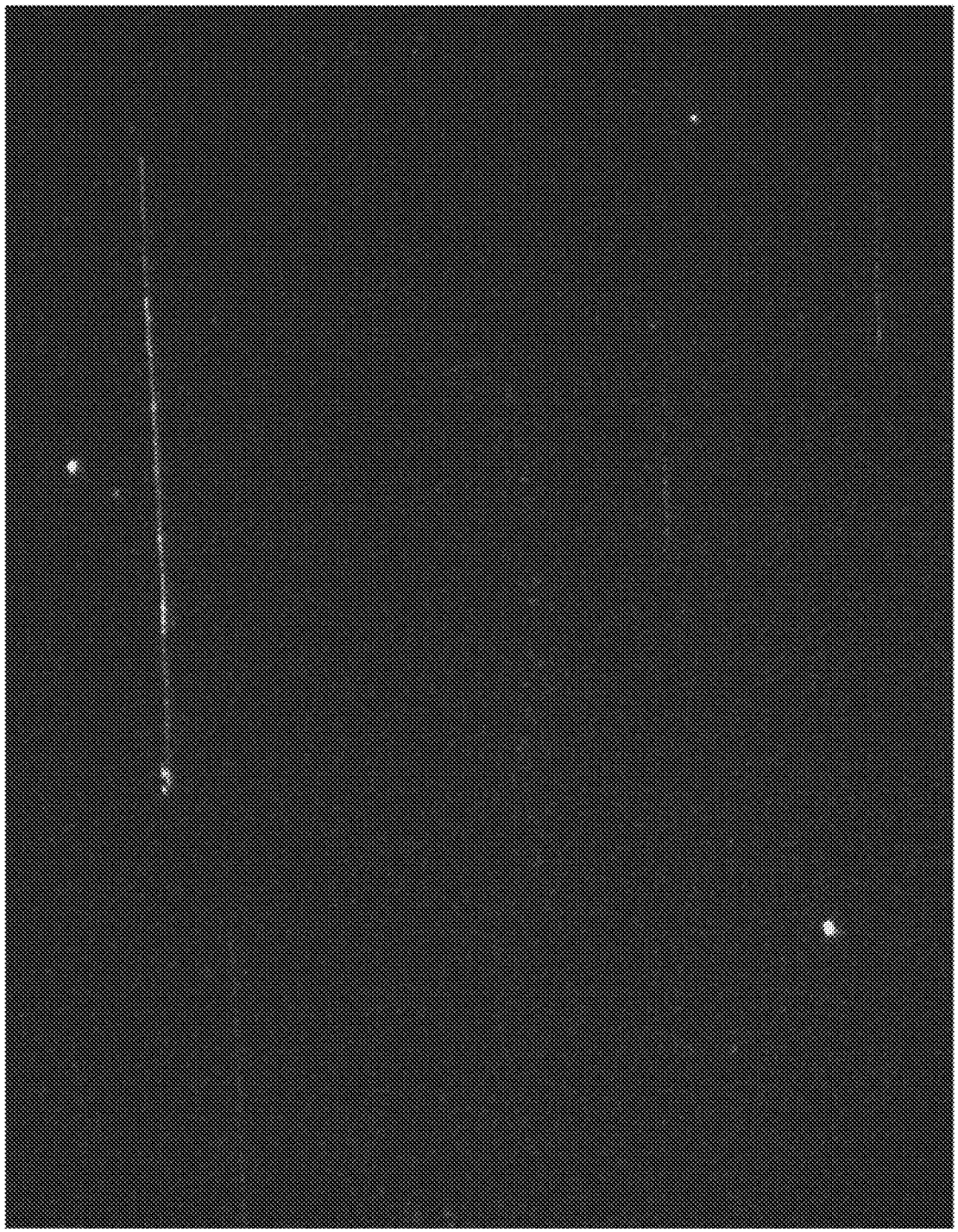
FIGS. 8A-8C are images of a set of stretched DNA templates, bound to a vinylsilane-coated coverslip, assembled to a flow cell, and then probed with fluorescently labeled Origami. The images were captured by fluorescent microscopy at 320× magnification.
Figure 8B:
Figure 8C:
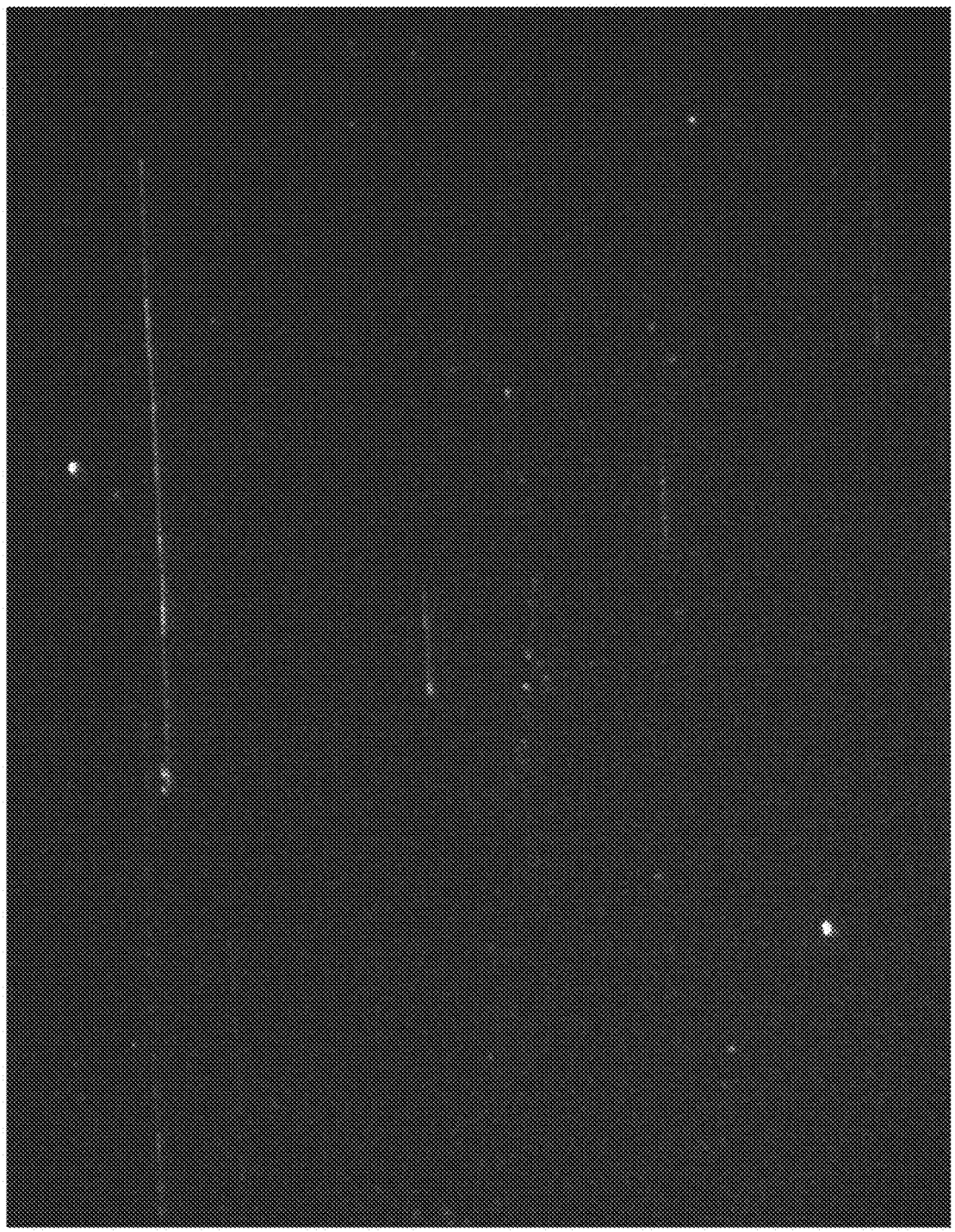

FIGS. 8A-8C are images of a set of stretched DNA templates, bound to a vinylsilane-coated coverslip, assembled to a flow cell, and then probed with fluorescently labeled Origami. The image was captured by fluorescent microscopy at 320× magnification. Top left: Green channel (CY3), top right: Red channel (CY5), bottom center: superposition of both channels.

Figure 9:
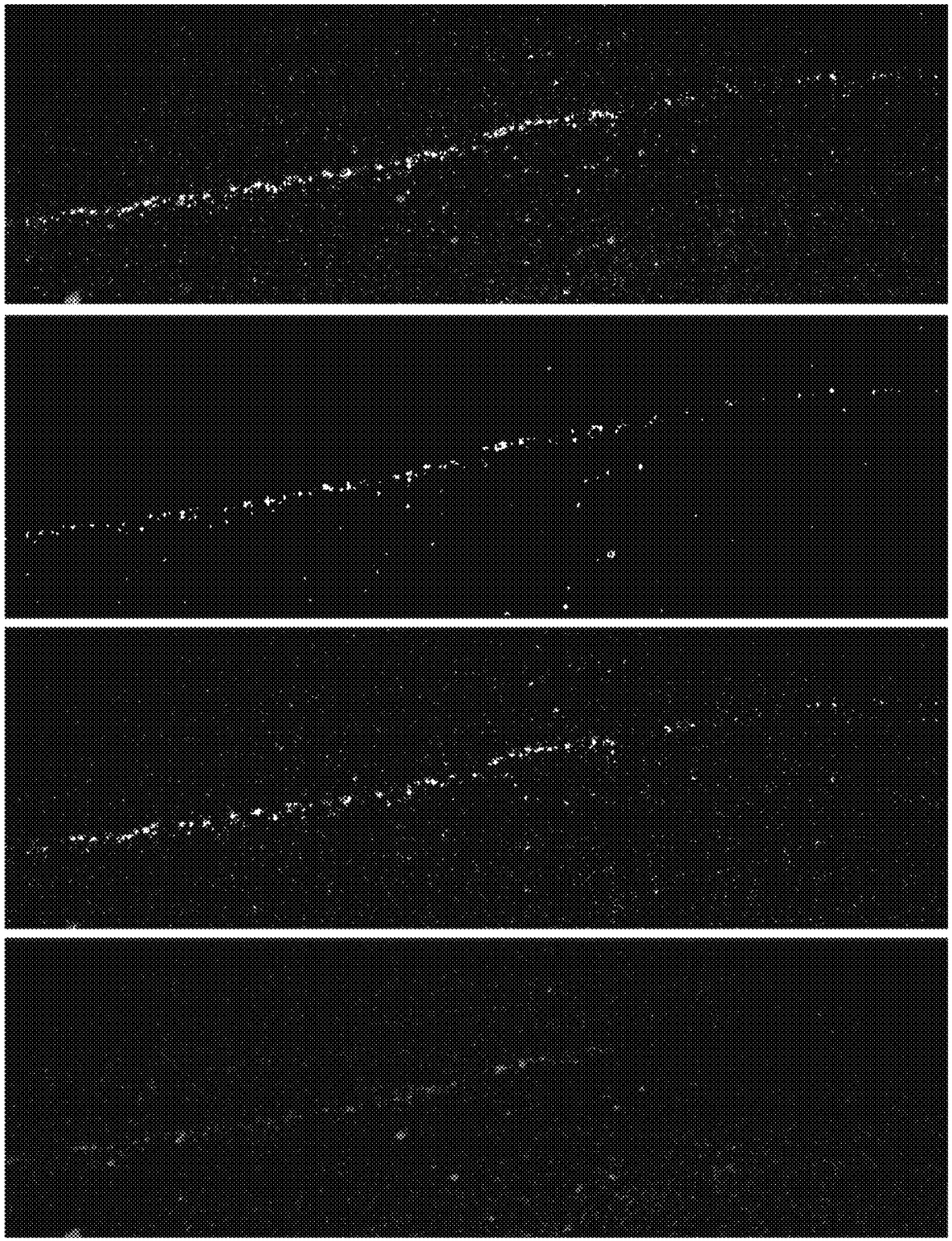
FIG. 9 are images of stretched DNA template, bound to a vinylsilane-coated coverslip, assembled to a flow cell, and then probed with a set of fluorescently labeled Origami, each specific to a different nucleic acid base, using T4 DNA ligase. The image was captured by fluorescent microscopy at 320× magnification. From left to right: Blue channel (FAM), Green channel (CY3), Red channel (CY5), and superposition of all three channels.

FIG. 9 are images of stretched DNA template, bound to a vinylsilane-coated coverslip, assembled to a flow cell, and then probed with a set of fluorescently labeled Origami, each specific to a different nucleic acid base, using T4 DNA ligase. The image was captured by fluorescent microscopy at 320× magnification. From left to right: Blue channel (FAM), Green channel (CY3), Red channel (CY5), and superposition of all three channels.

At higher resolution, by using super-resolution microscopy (Nikon STORM), a given Origami is labeled with multiple oligo-probes, creating a color barcode. This color code can be resolved to provide information about the sequence.

In another method, the linearized template is laid on a carbon grid to use with an electron microscope (JEOL JEM-1400), which provides the resolution to identify the Origami based on its shape, and then identify the nucleic acid sequence to which it corresponds. In this case, the Origami are labeled with 10 nm gold nanoparticles (AuNP) tagged with oligonucleotide complementary to the origami sequence. AuNP are first coated with 25 mM Phosphine (BSPP, Sigma) and are incubated overnight with gentle mixing. A 5M Sodium Chloride solution is then slowly added to the reaction until it turns to light purple. 100 µM Thiolated-oligo (IDT) were incubated in 20 mM TCEP (Sigma) for 30 minutes and purified using an Amicon Ultra 10 kDa column (Millipore). 100 µM oligo and 1 µM AuNP were then conjugated in Origami folding buffer (5 mM Tris-EDTA with 16 mM Magnesium Chloride) overnight, and purified in an Amicon Ultra 100 kDa column. 1 µL of 1 µM AuNP-DNA was added per 100 nM Origami and incubated overnight with gentle mixing. TEM images were generated following JEOL recommendation, typically using high voltage (100 kV).

The invention claimed is:

1. A method for identifying one or more nucleotides of a single stranded nucleic acid molecule, comprising:
   (a) providing said single stranded nucleic acid molecule comprising at least one nucleic acid probe coupled thereto, wherein said at least one nucleic acid probe includes a nucleic acid sequence complementary to said single stranded nucleic acid molecule and a spatially distinct nucleic acid structure, wherein said nucleic acid sequence is attached to said spatially distinct nucleic acid structure via a linker, wherein said spatially distinct nucleic acid structure is a folded configuration comprising a plurality of separate strands, and wherein said spatially distinct nucleic acid structure corresponds to one or more nucleotides of said at least one nucleic acid probe coupled to said single stranded nucleic acid molecule;
   (b) detecting one or more signals from said spatially distinct nucleic acid structure; and
   (c) using said one or more signals detected in (b) to identify said one or more nucleotides of said at least one nucleic acid probe, thereby identifying said one or more nucleotides of said single stranded nucleic acid molecule.

2. The method of claim 1, wherein in at least (a), said nucleic acid probe is coupled to an oligonucleotide molecule coupled to said single stranded nucleic acid molecule.

3. The method of claim 2, further comprising, prior to (a), bringing said single stranded nucleic acid molecule in contact with said oligonucleotide molecule under conditions sufficient to permit said oligonucleotide molecule to couple to said single stranded nucleic acid molecule.

4. The method of claim 3, further comprising, prior to (a), bringing said at least one nucleic acid probe in contact with said single stranded nucleic acid molecule comprising said oligonucleotide molecule coupled thereto, under conditions sufficient to permit said nucleic acid probe to couple to said single stranded nucleic acid molecule and said oligonucleotide molecule.

5. The method of claim 2, wherein said oligonucleotide molecule is a sequencing primer.

6. The method of claim 1, wherein said one or more signals are one or more optical signals.

7. The method of claim 1, wherein said at least one nucleic acid probe is a plurality of nucleic acid probes.

8. The method of claim 1, wherein said one or more nucleotides of said at least one nucleic acid probe are a plurality of nucleotides coupled to said single stranded nucleic acid molecule.

9. The method of claim 8, wherein said plurality of nucleotides comprises up to 100 nucleotides.

10. The method of claim 1, wherein said linker is a cleavable linker.

11. The method of claim 1, further comprising, prior to (b), straightening said single stranded nucleic acid molecule.

12. The method of claim 1, wherein said single stranded nucleic acid molecule is attached to a support.

13. The method of claim 1, wherein said folded configuration is a two-dimensional or three-dimensional structure.

14. The method of claim 1, wherein said one or more nucleotides of said at least one nucleic acid probe is one or more nucleotide analogs.

15. The method of claim 1, wherein said spatially distinct nucleic acid structure corresponds to a plurality of nucleotides of said at least one nucleic acid probe, which plurality of nucleotides is coupled to said single stranded nucleic acid molecule.

16. A composition for identifying one or more nucleotides of a single stranded nucleic acid molecule, comprising said single stranded nucleic acid molecule comprising at least one nucleic acid probe coupled thereto, wherein said at least one nucleic acid probe is coupled to an oligonucleotide molecule coupled to said single stranded nucleic acid molecule, wherein said at least one nucleic acid probe includes a spatially distinct nucleic acid structure, which spatially distinct nucleic acid structure is a folded configuration comprising a plurality of separate strands, and wherein said spatially distinct nucleic acid structure corresponds to one or more nucleotides of said nucleic acid probe coupled to said single stranded nucleic acid molecule.

17. The composition of claim 16, wherein said one or more nucleotides of said at least one nucleic acid probe are a plurality of nucleotides coupled to said single stranded nucleic acid molecule.

18. The composition of claim 16, wherein said one or more nucleotides of said at least one nucleic acid probe are part of a sequence of nucleotides coupled to said single stranded nucleic acid molecule, and wherein said spatially distinct nucleic acid structure is attached to said sequence of nucleotides via a linker.

19. The composition of claim 16, wherein said folded configuration is a two-dimensional or three-dimensional structure.

\* \* \* \* \*

SEQUENCE LISTING

```
<160> NUMBER OF SEQ ID NOS: 25

<210> SEQ ID NO 1
<211> LENGTH: 15
<212> TYPE: DNA
<213> ORGANISM: Artificial
<220> FEATURE:
<223> OTHER INFORMATION: sequencing primers
<220> FEATURE:
<221> NAME/KEY: misc_feature
<222> LOCATION: (1)..(15)
<223> OTHER INFORMATION: n is a, c, g, or t

<400> SEQUENCE: 1
nnnnnnnnnn nnnnn                                                  15

<210> SEQ ID NO 2
<211> LENGTH: 71
<212> TYPE: DNA
<213> ORGANISM: Artificial
<220> FEATURE:
<223> OTHER INFORMATION: synthesized oligonucleotide
<220> FEATURE:
```

```
<221> NAME/KEY: misc_feature
<222> LOCATION: (20)..(55)
<223> OTHER INFORMATION: n is a, c, g, or t

<400> SEQUENCE: 2
gttcctcatt ctctgaagan nnnnnnnnnn nnnnnnnnnn nnnnnnnnnn nnnnnacttc    60
agctgccccg g                                                        71

<210> SEQ ID NO 3
<211> LENGTH: 19
<212> TYPE: DNA
<213> ORGANISM: Artificial
<220> FEATURE:
<223> OTHER INFORMATION: adapters that will be used as a sequencing
      primer hybridization site (PS1)

<400> SEQUENCE: 3
gttcctcatt ctctgaaga                                                19

<210> SEQ ID NO 4
<211> LENGTH: 16
<212> TYPE: DNA
<213> ORGANISM: Artificial
<220> FEATURE:
<223> OTHER INFORMATION: adapters that will be used as a sequencing
      primer hybridization site (PS1)

<400> SEQUENCE: 4
acttcagctg ccccgg                                                   16

<210> SEQ ID NO 5
<211> LENGTH: 18
<212> TYPE: DNA
<213> ORGANISM: Artificial
<220> FEATURE:
<223> OTHER INFORMATION: bridge oligo

<400> SEQUENCE: 5
atgaggaacc cggggcag                                                 18

<210> SEQ ID NO 6
<211> LENGTH: 20
<212> TYPE: DNA
<213> ORGANISM: Artificial
<220> FEATURE:
<223> OTHER INFORMATION: RCA primer

<400> SEQUENCE: 6
aatgaggaac ccggggcagc                                               20

<210> SEQ ID NO 7
<211> LENGTH: 20
<212> TYPE: DNA
<213> ORGANISM: Artificial
<220> FEATURE:
<223> OTHER INFORMATION: RCA primer

<400> SEQUENCE: 7
aatgaggaac ccggggcagc                                               20

<210> SEQ ID NO 8
<211> LENGTH: 19
<212> TYPE: DNA
<213> ORGANISM: Artificial
<220> FEATURE:
<223> OTHER INFORMATION: dsDNA oligonucleotide adapter
```

-continued

```
<400> SEQUENCE: 8
gttcctcatt ctctgaaga                                               19

<210> SEQ ID NO 9
<211> LENGTH: 15
<212> TYPE: DNA
<213> ORGANISM: Artificial
<220> FEATURE:
<223> OTHER INFORMATION: dsDNA oligonucleotide adapter Ad2

<400> SEQUENCE: 9
tcttcagaga atgag                                                   15

<210> SEQ ID NO 10
<211> LENGTH: 16
<212> TYPE: DNA
<213> ORGANISM: Artificial
<220> FEATURE:
<223> OTHER INFORMATION: dsDNA oligonucleotide adapter Ad3

<400> SEQUENCE: 10
ccggggcagc tgaagt                                                  16

<210> SEQ ID NO 11
<211> LENGTH: 12
<212> TYPE: DNA
<213> ORGANISM: Artificial
<220> FEATURE:
<223> OTHER INFORMATION: dsDNA oligonucleotide adapter Ad4

<400> SEQUENCE: 11
acttcagctg cc                                                      12

<210> SEQ ID NO 12
<211> LENGTH: 19
<212> TYPE: DNA
<213> ORGANISM: Artificial
<220> FEATURE:
<223> OTHER INFORMATION: PCR primer

<400> SEQUENCE: 12
gttcctcatt ctctgaaga                                               19

<210> SEQ ID NO 13
<211> LENGTH: 16
<212> TYPE: DNA
<213> ORGANISM: Artificial
<220> FEATURE:
<223> OTHER INFORMATION: PCR primer

<400> SEQUENCE: 13
ccggggcagc tgaagt                                                  16

<210> SEQ ID NO 14
<211> LENGTH: 35
<212> TYPE: DNA
<213> ORGANISM: Artificial
<220> FEATURE:
<223> OTHER INFORMATION: adapter Ad5

<400> SEQUENCE: 14
gaagtcttct tactccttgg gccccgtcag acttc                             35

<210> SEQ ID NO 15
```

```
<211> LENGTH: 35
<212> TYPE: DNA
<213> ORGANISM: Artificial
<220> FEATURE:
<223> OTHER INFORMATION: adapter Ad6

<400> SEQUENCE: 15
gttccgagat tcctccgtt gttgttaatc ggaac                              35

<210> SEQ ID NO 16
<211> LENGTH: 18
<212> TYPE: DNA
<213> ORGANISM: Artificial
<220> FEATURE:
<223> OTHER INFORMATION: complementary oligonucleotide

<400> SEQUENCE: 16
taacaacaac ggaggaaa                                                18

<210> SEQ ID NO 17
<211> LENGTH: 19
<212> TYPE: DNA
<213> ORGANISM: Artificial
<220> FEATURE:
<223> OTHER INFORMATION: RCA primer

<400> SEQUENCE: 17
acggggccca aggagtaag                                               19

<210> SEQ ID NO 18
<211> LENGTH: 53
<212> TYPE: DNA
<213> ORGANISM: Artificial
<220> FEATURE:
<223> OTHER INFORMATION: template nucleotide and square origami
      structure
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 18
nnnnnnnnnn nnnnnccagt ngcgtcggaa ctcgtagtca actaatatga cgc         53

<210> SEQ ID NO 19
<211> LENGTH: 37
<212> TYPE: DNA
<213> ORGANISM: Artificial
<220> FEATURE:
<223> OTHER INFORMATION: template nucleotide and circular origami
      structure
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 19
nnnnnnnnnn nnnnngaacg ngcgtacttc taaacgc                           37

<210> SEQ ID NO 20
<211> LENGTH: 44
```

```
<212> TYPE: DNA
<213> ORGANISM: Artificial
<220> FEATURE:
<223> OTHER INFORMATION: template nucleotide and triangle origami
      structure
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 20
nnnnnnnnnn nnnnnttagt ngcgtgcgga ctcctaatat acgc                      44

<210> SEQ ID NO 21
<211> LENGTH: 104
<212> TYPE: DNA
<213> ORGANISM: Artificial
<220> FEATURE:
<223> OTHER INFORMATION: stretched ssDNA

<400> SEQUENCE: 21
tctatggcta cggtaggtca gtggtagcag tcggtgatcg atcctgactt gcggaaatgt     60
ccttgagaca cctagttggt aatcattaga gcggctcaga tcgc                     104

<210> SEQ ID NO 22
<211> LENGTH: 104
<212> TYPE: DNA
<213> ORGANISM: Artificial
<220> FEATURE:
<223> OTHER INFORMATION: stretched ssDNA

<400> SEQUENCE: 22
tctatggcta cggtaggtca gtggtagcag tcggtgatcg atcctgactt gcggaaatgt     60
ccttgagaca cctagttggt aatcattaga gcggctcaga tcgc                     104

<210> SEQ ID NO 23
<211> LENGTH: 73
<212> TYPE: DNA
<213> ORGANISM: Artificial
<220> FEATURE:
<223> OTHER INFORMATION: template nucleotide and square origami
      structure with detectable labels Cy5, Cy3, and TR
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 23
nnnnnnnnnn nnnnnccagt ngcgtcggaa gaactcggta agccgtaacg tacgtagtca     60
actaatatga cgc                                                        73

<210> SEQ ID NO 24
<211> LENGTH: 73
<212> TYPE: DNA
<213> ORGANISM: Artificial
<220> FEATURE:
<223> OTHER INFORMATION: template nucleotide and square origami
      structure with detectable labels FITC, Cy3, and TR
<220> FEATURE:
<221> NAME/KEY: misc_feature
```

```
<222> LOCATION: (1)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 24
nnnnnnnnnn nnnnngaacg ngcgtcggaa gaactcggta acccgtaacg tacgtagtca        60
actaatatga cgc                                                          73

<210> SEQ ID NO 25
<211> LENGTH: 21
<212> TYPE: DNA
<213> ORGANISM: Artificial
<220> FEATURE:
<223> OTHER INFORMATION: template nucleotide and origami probe
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 25
nnnnnnnnnn nnnnnttagt n                                                 21
```